(12) United States Patent
Tsurukawa et al.

(10) Patent No.: US 9,173,478 B2
(45) Date of Patent: Nov. 3, 2015

(54) ORAL CARE INSTRUMENT

(75) Inventors: Naoki Tsurukawa, Takatsuki (JP); Seiji Tokuoka, Takatsuki (JP); Masafumi Hamada, Fujioka (JP); Satoru Sumiyoshi, Fujioka (JP)

(73) Assignee: SUNSTAR INC., Takatsuki-shi (JP)

( * ) Notice: Subject to any disclaimer, the term of this patent is extended or adjusted under 35 U.S.C. 154(b) by 927 days.

(21) Appl. No.: 13/375,967

(22) PCT Filed: Jun. 3, 2010

(86) PCT No.: PCT/JP2010/059448
§ 371 (c)(1),
(2), (4) Date: Dec. 2, 2011

(87) PCT Pub. No.: WO2010/140660
PCT Pub. Date: Dec. 9, 2010

(65) Prior Publication Data
US 2012/0077145 A1 Mar. 29, 2012

(30) Foreign Application Priority Data
Jun. 4, 2009 (JP) ................................. 2009-135563

(51) Int. Cl.
*A46B 11/00* (2006.01)
*A46B 5/00* (2006.01)
*A46B 7/04* (2006.01)
*A61C 5/06* (2006.01)
*A61C 19/06* (2006.01)

(52) U.S. Cl.
CPC ............ *A46B 11/0027* (2013.01); *A46B 5/0095* (2013.01); *A46B 7/04* (2013.01); *A46B 11/0086* (2013.01); *A46B 11/0089* (2013.01); *A46B 2200/108* (2013.01); *A61C 5/062* (2013.01); *A61C 19/063* (2013.01)

(58) Field of Classification Search
USPC .......... 401/270, 277, 282, 284, 290; 300/2, 5, 300/7, 8
See application file for complete search history.

(56) References Cited

U.S. PATENT DOCUMENTS 5,148,568 A * 9/1992 Bojar et al. ........................ 15/28
6,186,782 B1 * 2/2001 Luppi .............................. 433/82

FOREIGN PATENT DOCUMENTS

| JP | 7-33679 | 6/1995 |
| JP | 10-52447 | 2/1998 |
| JP | 11-509470 | 8/1999 |

(Continued)

OTHER PUBLICATIONS

International Search Report for International Application No. PCT/JP2010/059448 dated Jul. 6, 2010.

*Primary Examiner* — David Walczak
(74) *Attorney, Agent, or Firm* — Kratz, Quintos & Hanson, LLP

(57) ABSTRACT

An oral care instrument, which can maintain a sufficient support strength of a long neck, leaves little residue of a medicant after using, has a low contamination risk from nozzle tip, allows smooth spouting of a medical solution from the beginning, prevents excessive supply of gelatinous or creamy oral-care composition in the case of flowing the composition in a supply channel inside the same, and contributes to the maintenance of the durability of a manufacturing mold. In the aforesaid oral care instrument, which comprises a handle (2), a head (3) and a neck (4), a channel (11) for supplying oral-care composition running within the neck (4) to a nozzle (10) of the head (3) via the handle (2), is formed; and the head (3) is connected in a detachable manner to the neck (4).

10 Claims, 17 Drawing Sheets

(56) References Cited

FOREIGN PATENT DOCUMENTS

| JP | 11-276508 | 10/1999 |
| JP | 2007-501651 A1 | 2/2007 |
| JP | 2007-167088 A1 | 7/2007 |
| JP | 2008-501412 A1 | 1/2008 |
| JP | 2008-132099 A1 | 6/2008 |

* cited by examiner

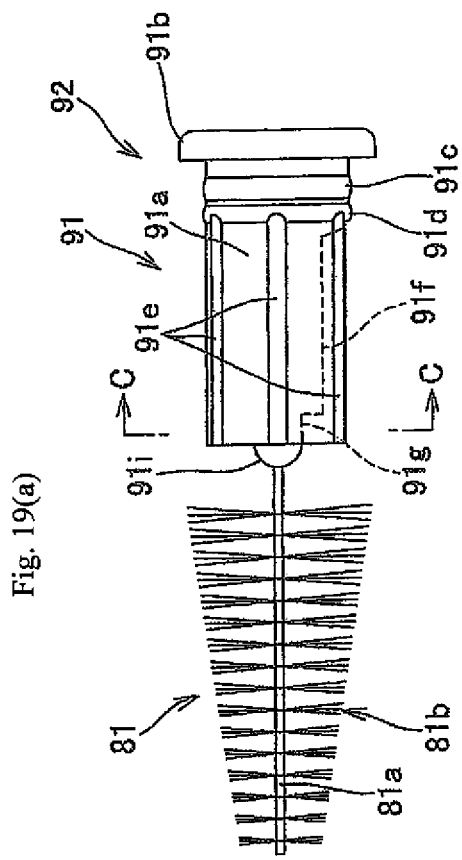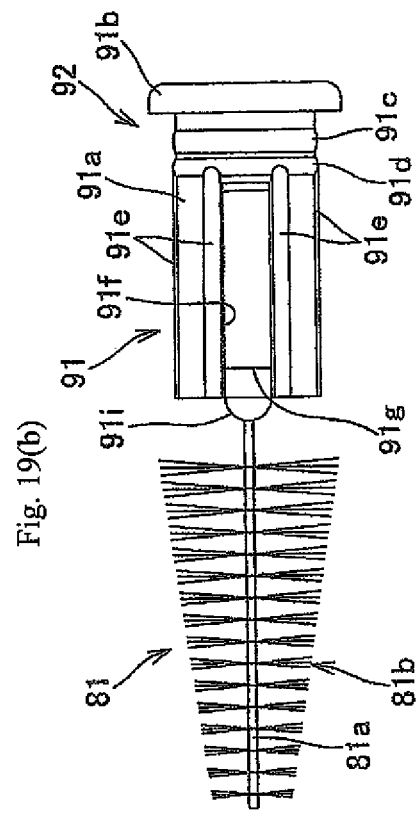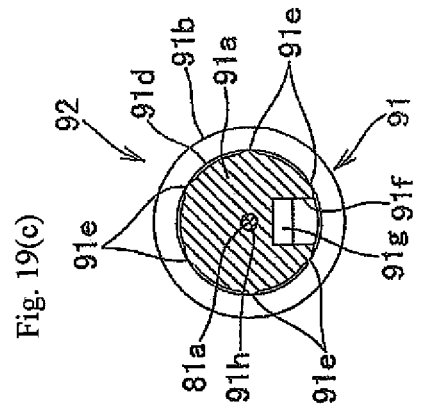

Fig. 22
(a)
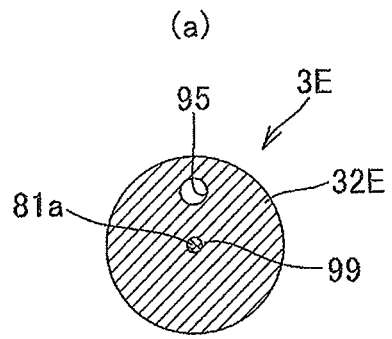
(b)
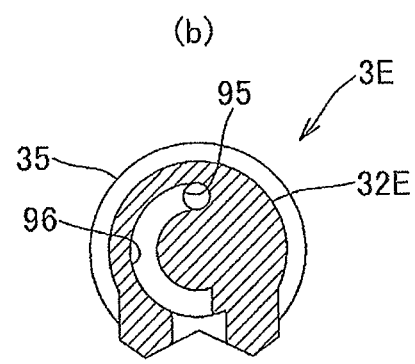
(c)
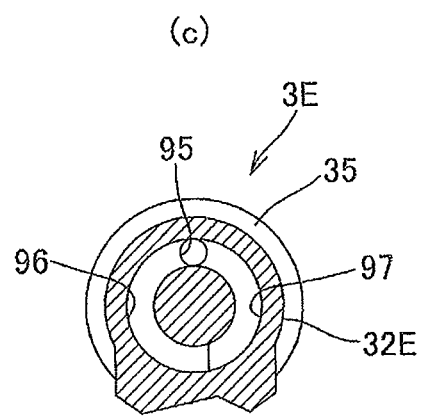

ORAL CARE INSTRUMENT

TECHNICAL FIELD

The present invention relates to an oral care instrument for applying an oral composition in an oral cavity by discharging the oral composition from a nozzle portion at a distal end of the oral care instrument.

BACKGROUND ART

As an oral care instrument of this type, there is conventionally proposed an oral care instrument which includes washing solution supply means, and a long washing solution discharge tube attached to the washing solution supply means (for example, see Japanese Unexamined Patent Publication No. 2007-167088). In this oral care instrument disclosed in Japanese Unexamined Patent Publication No. 2007-167088, an elastic nozzle is provided at a distal end of the washing solution discharge tube, and the washing solution supply means is composed of a washing solution container having a pumping function. In addition, every time a pressing portion (button) provided on the washing solution container is pressed, the washing solution is ejected from a discharge orifice opened to a projecting end of the elastic nozzle provided at the distal end of the washing solution discharge tube through a discharge flow path in the washing solution discharge tube. Further, there is also proposed another oral care instrument which also includes washing solution supply means, and a washing solution discharge tube attached to the washing solution supply means (for example, see Japanese Unexamined Patent Publication No. 2008-132099). The oral care instrument disclosed in Japanese Unexamined Patent Publication No. 2008-132099 further includes a cleaning member, and a washing solution ejecting portion. The cleaning member is provided at a distal end of the washing solution discharge tube so as to be projected in the direction perpendicular to the axial direction of the washing solution discharge tube. The washing solution ejecting portion has a washing solution discharge orifice which communicates with a discharge flow path of the washing solution discharge tube, is opened to the external side with respect to a position in the vicinity of the base of the cleaning member, and ejects washing solution toward the projection of the cleaning member from the middle portion to the distal end thereof.

According to the oral care instrument disclosed in Japanese Unexamined Patent Publication No. 2007-167088, the washing solution can be accurately ejected toward an interdental portion with less washing solution scattered, and food debris can be surely removed from the interdental portion with the washing solution for washing. According to the oral care instrument disclosed in Japanese Unexamined Patent Publication No. 2008-132099, after dental plaque which cannot be removed with water flow only is removed with the cleaning member, the washing solution can be effectively supplied to deep portions through the cleaning member. This makes it possible to effectively sterilize and suppress inflammation of a tissue by supplying drug solution containing an antimicrobial agent, an anti-inflammatory agent, or the like to embrasures, gingival marginal portions, periodontal pockets, or the like.

However, in these conventional oral care instruments, components from the washing solution discharge tube to the nozzle portion ejecting the washing solution are integrally formed. Further, since the washing solution discharge tube is required to have strength enough to support forces received from the elastic nozzle or the cleaning member when used by a user, the washing solution discharge tube is required to have a certain size in diameter. Moreover, if the thickness of the washing solution discharge tube is decreased in consideration of the material cost, an internal space thereof is made larger to some extent. If the internal space is made larger as described above, there arise a problem that the drug solution is hard to be ejected at the start of use, and a problem that the amount of remaining drug after use is large and the risk of being contaminated from the distal end of the nozzle is increased. On the other hand, if the internal space is made too small, durability of a produced mold is made worse, and the following problem is caused. The problem is that when the gel or cream oral composition flows through the internal space of the washing solution discharge tube as a supply path, the oral composition transmitted to the supply path does not stop immediately even when the transmitting operation is stopped and thus an excess amount of the oral composition are ejected and wasted.

CITATION LIST

Patent Literature

Patent Document 1: Japanese Unexamined Patent Publication No. 2007-137088
Patent Document 2: Japanese Unexamined Patent Publication No. 2008-132099

SUMMARY OF INVENTION

Technical Problem

The present invention has been made in consideration of the above circumstances. An object of the present invention is to provide an oral care instrument in which a long neck portion keeps a sufficient supporting strength, the amount of remaining drug after use is small, the risk of being contaminated from the distal end of the nozzle is decreased, and the drug solution is easily ejected at the start of use. At the same time, in the oral care instrument, the excess amount of the gel or cream oral composition are prevented from being ejected when the oral composition is flown through the internal supply path, while the durability of the produced mold can be maintained.

Solution to Problem

In order to solve the above-described problems, according to the present invention, there is provided an oral care instrument for applying a gel or cream oral composition in an oral cavity by discharging the oral composition from a nozzle portion at a distal end of the instrument, including: a handle body gripped when used; a head body having the nozzle portion for discharging the oral composition at the distal end of the instrument; and a neck body which is formed between the handle body and the head body and by which the head body can be inserted to deep portions in the oral cavity, wherein a supply path for supplying the oral composition from the handle body to the nozzle portion of the head body through an inner side of the neck body is provided, and the head body is detachably coupled to the neck body (first aspect of the invention).

Further, in the oral care instrument, it is preferable that a plurality of ribs which are projected in the direction of a center axis and are extended long in the axial direction are provided on an inner circumferential wall of the neck body, and a cylindrical tube member which has an inner diameter of 1 to 2 mm and constitutes the supply path of the oral composition is inserted and attached to the neck body in such a manner that an outer circumferential face of the tube member is supported by the plurality of ribs (second aspect of the invention).

Further, in the oral care instrument, it is preferable that an application member formed of a bundle of filaments is provided at the nozzle portion of the head body (third aspect of the invention).

Specifically, in the oral care instrument, it is preferable that the application member is formed of only one bundle of filaments (fourth aspect of the invention).

Further, in the oral care instrument, it is preferable that a base on which a plurality of filaments constituting the bundle are integrally fused with each other at base ends of the filaments and which is swelled outward is provided on the application member, a communicating hole communicating with an opening of the nozzle portion is provided on the base, and a ring stopper member for the application member which is attached from the distal end side of the application member to the exterior of the application member so as to be locked to the swelled portion of the base is attached together with the application member to the circumference of the nozzle portion of the head body (fifth aspect of the invention).

Further, in the oral care instrument, it is preferable that a brush body for cleaning interdental spaces is provided at a distal end of the head body instead of the application member, and the nozzle portion is opened toward a brush portion of the brush body (sixth aspect of the invention).

When the brush body for cleaning interdental spaces is provided in the oral care instrument, it is preferable that the head body is formed into a bent shape (seventh aspect of the invention).

Further, in the oral care instrument, it is also possible that an interdental brush member having the brush body and a brush supporting portion for supporting the brush body is provided, the interdental brush member being a separate member from the head body, and an attachment portion for externally holding the brush supporting portion is provided at the distal end of the head body (eighth aspect of the invention).

When the interdental brush member which is a separate member from the head body is provided, it is preferable that a locking portion swelled outward is formed at a base portion of the brush supporting portion, and a ring stopper member is provided so as to be externally fitted to the brush supporting member and internally fitted and fixed to the attachment portion, so that an end portion of the stopper member can be engaged with the locking portion (ninth aspect of the invention).

Further, when the interdental brush member which is a separate member from the head body is provided, it is possible that a communication path communicating with a supply path of the head body is formed on the brush supporting portion, and a nozzle portion is formed at an end portion of the communication path (tenth aspect of the invention).

Furthermore, when the brush body is integrally provided in the head body, it is preferable that the head body is formed into a bent shape, a base side supply path and a distal end side supply path of the head body are formed at an angle to each other, the distal end side supply path of the head body is formed by a through hole passing through a distal end side portion of the head body, a lid member for occluding an opening at a base end of the through hole is fixed to a base of the distal end side portion of the head body (eleventh aspect of the invention).

Moreover, it is preferable that the oral care instrument includes a cap detachably attached to each of a position at which the nozzle portion at the distal end side of the head body is covered and a position at which a distal end of the neck body is covered in a state where the head body is detached (twelfth aspect of the invention).

Further, in the oral care instrument, it is preferable that the head body is formed into a substantially dog-leg shape, a plurality of projections are provided on the outer circumferential face of the distal end of the neck body with intervals in the circumferential direction, convex portions which is engaged with concave grooves formed between the projections are provided at corresponding positions to the distal end of the neck body on the inner circumferential wall of the head body, and when the distal end of the neck body is inserted and coupled to the head body, the convex portions are engaged with the projections, resulting in as a stopper of the rotation (thirteenth aspect of the invention).

Further, in the oral care instrument, it is preferable that one or both of side ends on the projections at the distal end side of the neck body in the axial direction and side ends on the convex portions at the base end side of the head body in the axial direction are formed in a V tapered shape, the side ends on the projections and the side ends on the convex portions being opposed to each other in the axial direction when coupled (fourteenth aspect of the invention).

Further, in the oral care instrument, it is preferable that a container containing the oral composition and a screw type transmission mechanism for pushing the oral composition out to a supply path are provided inside of the handle body (fifteenth aspect of the invention).

Advantageous Effects of Invention

In the oral care instrument according to the present invention configured as described above, the supply path for supplying the oral composition from the handle body to the nozzle portion of the head body through the inner side of the neck body is provided and the head body is detachably coupled to the neck body. This makes it possible to wash and dry the nozzle portion at the distal end or the like by detaching the head body after used so that the good oral care instrument in terms of a hygiene viewpoint is obtained.

In the oral care instrument, a plurality of ribs which are projected in the direction of a center axis, and are extended long in the axial direction are provided on the inner circumferential wall of the neck body. A cylindrical tube member which has an inner diameter of 1 to 2 mm and constitutes the supply path of the oral composition is inserted and attached to the neck body in such a manner that the outer circumferential face of the tube member is supported by the plurality of ribs. Accordingly, even if the outer diameter or thickness of the neck body is made smaller, a sufficient strength can be obtained and the insertability to details in the oral cavity can be improved. Further, the supply path can be made to have a required minimum size of a cross-sectional area by setting a size of the tube member, thereby preventing an excess amount of the oral composition from being supplied.

In other words, since the neck body is required to have strength enough to support forces received from the head body in use, the neck body is required to have a certain size in diameter. Further, if the thickness of the neck body is decreased in consideration of the material cost, an internal space thereof is made larger. Conventionally, it is believed that the oral composition can be flown through the internal space itself as a supply path. However, if the supply path is wide beyond necessity, there arise a problem that the drug solution is hard to be ejected at the start of use, and a problem that the amount of remaining drug after use is large and the risk of being contaminated from the distal end of the nozzle is increased. On the other hand, if the supply path is made smaller at the time of forming the supply path, the strength and durability of a produced mold is made worse, and the following problem is caused at the same time. The problem is that the oral composition pushed out to the supply path does not stop immediately even when the pushing operation is stopped and an excess amount of the oral composition are ejected and wasted, although depending on rheological characterization of the oral composition. In order to solve the problems, a plurality of ribs are projected to the inner circumferential face and a tube member is provided at an inner side of the ribs to make a supply path in the invention. With the ribs provided, even if the outer diameter and thickness of the neck body are made smaller, a sufficient strength can be obtained. At the same time, since the oral composition is supplied through the tube member at the inner side of the ribs, a cross-sectional area of the tube member can be appropriately set in accordance with the rheological characterization of the oral composition, thereby preventing an excess amount of the oral composition from being supplied.

Even in a case where the neck body is injection-molded by a synthetic resin, since a convex and concave configuration for forming ribs is provided on a mold forming an internal space, durability and strength of the mold can be maintained so that the neck body having small outer diameter and thickness can be formed at high accuracy. Further, an operation in which the tube member separately formed is mounted in the neck body can be easily performed without fail, and an assembling operation can be easy. That is because when the tube member is inserted to be attached, the tube member is supported and guided by the above ribs so that the tube member can be located at a center position at which an axis of the tube member matches to that of the neck portion by simply pushing the tube member, and the contact area causing a resistance when inserted is small.

Moreover, an application member formed of a bundle of filaments is provided at the nozzle portion of the head body. This makes it possible to apply the oral composition to or into detailed sites in the oral cavity. Therefore, the oral composition can be also applied after the contaminants are cleaned with a bundle of filaments.

In addition, since the application member is formed of only one bundle of filaments, the application member can be easily produced and an operation of applying the oral composition to or into detailed sites in the oral cavity when used is effectively performed.

Further, in the instrument, a base on which a plurality of filaments constituting the bundle are integrally fused with each other at base ends of filaments and which is swelled outward is provided on the application member, a communicating hole communicating with an opening of the nozzle portion is provided on the base, and a ring stopper member for the application member which is attached from the distal end side of the application member to the exterior of the application member so as to be locked to the swelled portion on the base is attached together with the application member to the circumference of the nozzle portion of the head body. Since the application member, formed of the bundle, is attached to the circumference of the nozzle portion while being bound by the ring stopper member for the application member, the filaments can be prevented from being fallen, and the manufacturing can be easily and effectively performed only by integrally assembling the application member stopper member and the application member to the head body.

Further, in the oral care instrument, a brush body for cleaning interdental spaces is provided at the distal end of the head body instead of the application member and the nozzle portion is opened toward a brush portion of the brush body. This makes it possible to clean interdental spaces while applying the oral composition to the interdental spaces by cleaning the interdental spaces with the brush body after discharging the oral composition to the brush portion. In addition, it becomes also possible to apply the oral composition to interdental spaces with the brush body by discharging the oral composition to the brush portion after cleaning the interdental spaces with the brush body.

Further, in the oral care instrument, when the brush body for cleaning interdental spaces is provided, the head body is formed into a bent shape. With this configuration, it is possible to smoothly carry out a cleaning operation especially with respect to back teeth.

Further, in the oral care instrument, an interdental brush member having the brush body and a brush supporting portion for supporting the brush body is provided, the interdental brush member being a separate member from the head body, and an attachment portion for externally holding the brush supporting portion is provided at the distal end of the head body. Accordingly, when the brush body is damaged, a new brush body can be attached by replacing only the interdental brush member composed of the brush body and the brush supporting portion. Therefore, an economic burden of a user can be reduced in comparison with a case where the brush body needs to be replaced together with the head body and the neck body.

Further, in the oral care instrument, when the interdental brush member which is a separate member from the head body is provided, a locking portion swelled outward is formed at the base portion of the brush supporting portion, and a ring stopper member is provided so as to be externally fitted to the brush supporting member and internally fitted and fixed to the attachment portion, so that the end portion of the stopper member can be engaged with the locking portion. In this case, although the number of parts is increased, it is preferable since the detachment of the interdental brush member from the attachment portion of the head body can be effectively prevented. In the interdental brush member, the angle of the brush portion is adjusted by bending the core member at the vicinity of the main body portion. Therefore, it is preferable that the main body portion is made of a synthetic resin material which is softer than the head body in order to prevent the core member from being fractured at the bent portion and increase the durability of the interdental brush member. However, when the main body portion is made of a soft synthetic resin material in this way, the main body portion becomes more likely to be elastically deformed, thereby resulting in that the pullout strength of the interdental brush member is decreased when the main body portion is directly fitted and fixed to the attachment portion. On the other hand, in the present invention, since the stopper member can be made of a hard synthetic resin material as with the head body, the pullout strength of the stopper member with respect to the head body can be sufficiently ensured. In addition to this, also in the main body portion, the pullout strength of the main body portion can be easily and sufficiently ensured by virtue of the engagement between the locking portion swelled outward and the base end of the stopper member. Therefore, it is possible to effectively prevent the interdental brush member from being detached from the attachment portion of the head body.

Further, in the oral care instrument, when the interdental brush member which is a separate member from the head body is provided, a communication path communicating with a supply path of the head body is formed on the brush supporting portion, and a nozzle portion is formed at the end portion of the communication path. This makes it possible to discharge the oral composition to the brush body.

Further, in the oral care instrument, when the brush body is integrally provided in the head body, it is also possible that the head body is formed into a bent shape, a base side supply path and a distal end side supply path of the head body are formed at an angle to each other, the distal end side supply path of the head body is formed by a through hole passing through a distal end side portion of the head body, a lid member for occluding an opening at a base end of the through hole is fixed to a base of the distal end side portion of the head body. In this case, since the head body is formed into a bent shape, it is possible to improve the insertion operability of the brush body into interdental spaces and smoothly carry out a cleaning operation especially with respect to back teeth. Further, although the brush body needs to be replaced together with the head body, it is possible to reliably prevent the brush body from being detached from the head body since the brush body can be firmly fixed to the head body. Furthermore, since the distal end side supply path of the head body is formed by the through hole, the formability of the supply path can be sufficiently ensured.

Further, the oral care instrument includes a cap detachably attached to each of a position at which a nozzle portion at the distal end side of the head body is covered and a position at which a distal end of the neck body is covered in a state where the head body is detached. With the cap, desiccation of the oral composition (volatilization of water or drug) can be prevented while protecting the application portion and the like by covering the cap on the distal end of the head body when the instrument is not used. When the neck body is detached from the head body to wash, dry, or the like the head body, the same cap is attached to the neck body so that the handle body and the neck body can be stored in a state where the head body is detached while similarly preventing desiccation of the oral composition. The sealing performance (virgin performance) until a first use can be assured. When the head body is assembled again, the head body is attached by detaching the cap from the neck body and the same cap is attached to the nozzle portion of the head body. Therefore, the cap is effective and convenient component. Specifically, when the bundle of filaments is provided as the application member of the nozzle portion, the bundle is covered with the cap in a closely sealed manner so as to prevent desiccation of the bundle. In consideration of this point, as the material of the bundle of filaments, nylon resin can be used, but a PTB resin, PPT resin, or a PPT/PBT resin having low water absorbability is preferably used in order to prevent the deterioration of the physical property of filaments by water absorption. Further, it is also preferable to use filaments which have been subjected to an antimicrobial treatment from a hygiene point of view.

Further, in the oral care instrument, the head body is formed into a substantially dog-leg shape, a plurality of projections are provided on the outer circumferential face of the distal end of the neck body with intervals in the circumferential direction, convex portions which is engaged with concave grooves formed between the projections are provided at corresponding positions to the distal end of the neck portion on the inner circumferential wall of the head body, and when the distal end of the neck body is inserted and coupled to the head body, the convex portions are engaged with the projections, resulting in as a stopper of the rotation. Therefore, even if a force is applied to the head portion when the head portion is pushed against sites in the oral cavity, or the like, the head portion does not rotate and is hold at a position with a certain angle. Therefore, the oral composition can be effectively applied to even anterior teeth or molars without fail by pushing the head portion against the sites in the oral cavity.

Further, in the oral care instrument, one or both of side ends on the projections at the distal end side of the neck body in the axial direction and side ends on the convex portions at the base end side of the head body in the axial direction are formed in a V tapered shape, the side ends on the projections and the side ends on the convex portions being opposed to each other in the axial direction when coupled. Therefore, a problem that the projections and the convex portions cannot be fitted to each other successfully or fitted to each other insufficiently because they hit each other can be avoided so that attachment and detachment operations can be easily performed without fail. That is to say, the user can easily perform attachment and detachment operations of the head body without fail when the user detaches the head body for washing and the like, and the detachment of the head body during use because of the insufficient fitting can be prevented.

Further, in the oral care instrument, a container containing the oral composition and a screw type transmission mechanism for pushing the oral composition out to a supply path are provided inside the handle body. With the screw type transmission mechanism, only necessary amount of the gel or cream oral composition can be accurately ejected for use with light force for the operation thereof.

BRIEF DESCRIPTION OF DRAWINGS

FIG. 19(a) is a plan view and FIG. 19(b) is a front view of the interdental brush member of the oral care instrument in FIG. 17, and FIG. 19(c) is a cross-sectional view cut along a line C-C in FIG. 19(a).

FIG. 22(a) is a cross-sectional view cut along a line A-A in FIG. 20, FIG. 22(b) is a cross-sectional view cut along a line B-B in FIG. 20, and FIG. 22(c) is a cross-sectional view cut along a line C-C in FIG. 20.

DESCRIPTION OF EMBODIMENTS

Hereinafter, an embodiment of the present invention is described in detail with reference to the accompanying drawings.

Figure 1:
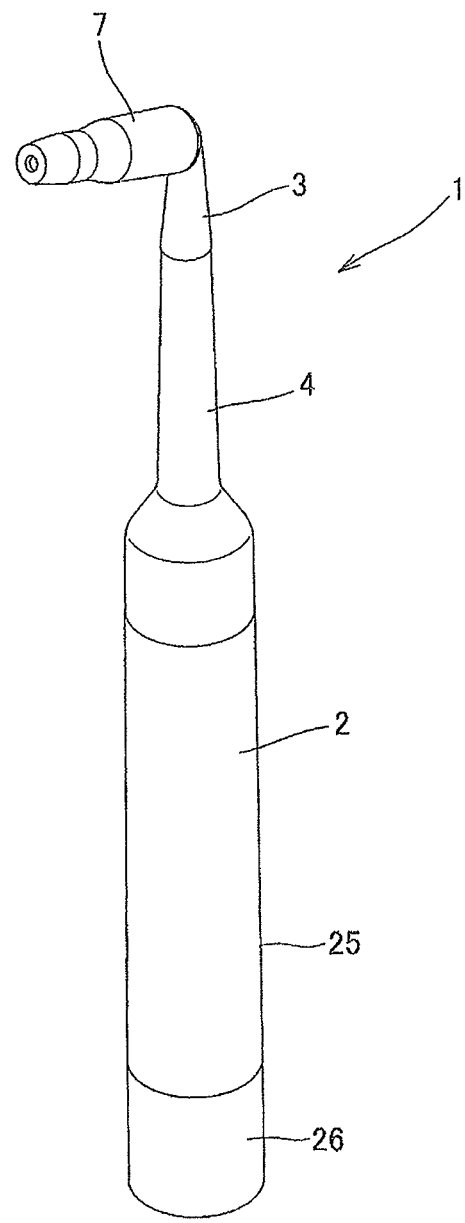
FIG. 1 is a perspective view illustrating an overall configuration of an oral care instrument according to a representative embodiment of the present invention.
Figure 2:
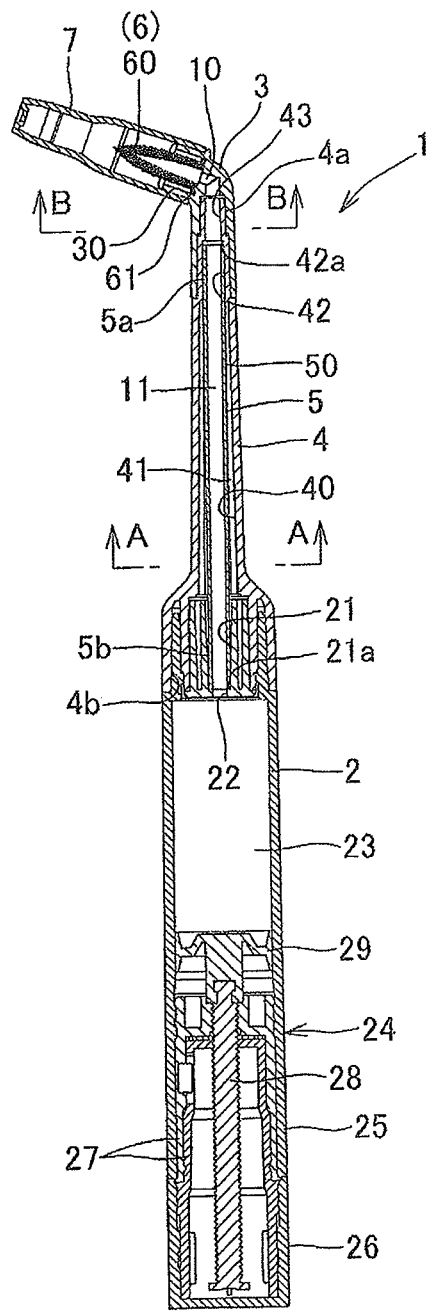
FIG. 2 is a longitudinal cross-sectional view of the oral care instrument in FIG. 1.

FIG. 1 is a perspective view illustrating an overall configuration of an oral care instrument according to the invention, and FIG. 2 is a longitudinal cross-sectional view in which a distal end side from a handle body 2 is fractured partially. FIGS. 1 to 8 show a representative embodiment of the invention. In the drawings, reference numeral 1 indicates the oral care instrument, 2 indicates the handle body, 3 indicates a head body, and 4 indicates a neck body.

As shown in FIGS. 1 and 2, the oral care instrument 1 is an instrument for applying a gel or cream oral composition in an oral cavity by discharging the oral composition from a nozzle portion 10 at a distal end of the oral care instrument 1. The oral care instrument 1 includes the handle body 2 gripped by a user when used, the head body 3 having the nozzle portion 10 for discharging the oral composition to the distal end side, the neck body 4 which is attached between the handle body 2 and the head body 3. The neck body 4 is long in the axial direction so as to insert the head body 3 to deep portions in the oral cavity. In the oral care instrument 1 according to the invention, it is characterized in that an oral composition supply path 11 is provided from the handle body 2 to the nozzle portion 10 of the head body 3 through the inner side of the neck body 4, and the head body 3 is detachably coupled to the neck body 4.

Figure 8:
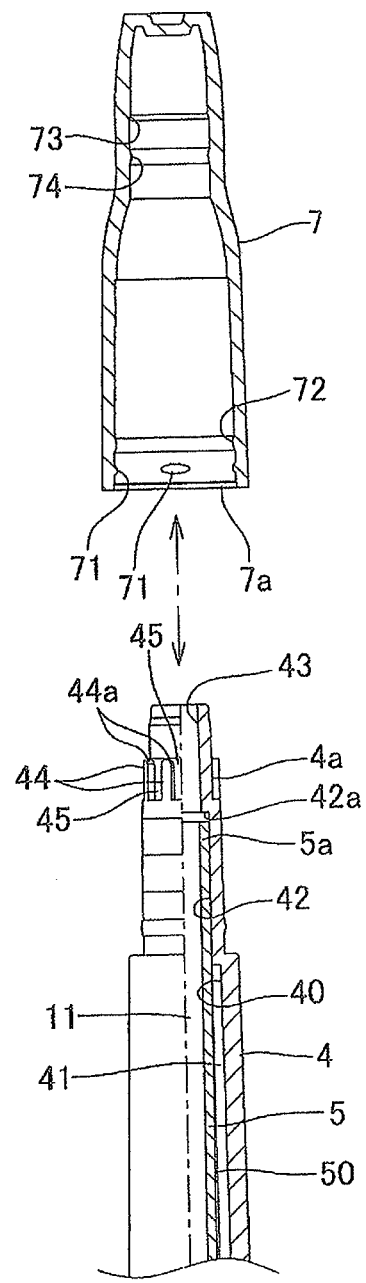
FIG. 8 is a longitudinal cross-sectional view illustrating a coupling configuration in which the cap is attached to a distal end of the neck body in the oral care instrument in FIG. 1.

In the embodiment described below, a cap 7 is provided at a distal end of the head body 3 so as to occlude the nozzle portion 10, and the same cap 7 can be attached to a distal end of the neck body 4 when the head body 3 is detached from the neck body 4 as shown in FIG. 8. However, the cap 7 may be omitted or a cap dedicated only to the head body 3 or different caps dedicated to each of the head body 3 and the neck body 4 may be provided.

A container 23 containing the oral composition, and a screw type transmission mechanism 24 for pushing the oral composition out to the supply path 11 are provided inside the handle body 2. The screw type transmission mechanism 24 of the embodiment has a configuration same as a liquid pressurizing mechanism disclosed in Japanese Unexamined Patent Publication No. 2007-330814. To be more specific, the screw type transmission mechanism 24 has a mechanism as follows. A piston body 29 fixed to a distal end of a threaded bar 28 pushes the oral composition in the container 23 out by moving the threaded bar 28 in the axial direction through a holding member 27. Here, a rotational operation member 26 rotatable with respect to a main body 25 is provided at a base end of the handle body 2, and the holding member 27 is coupled to the rotational operation member 26 so as to integrally rotate with the rotational operation member 26. A ratchet is formed at an engagement portion of the holding member 27 and the rotational operation member 26 so that the holding member 27 is integrally rotated in only one direction with the rotational operation member 26. The threaded bar 28 is threaded to an internal thread formed in a hollow at a center portion of the holding member 27. When the rotational operation member 26 rotates in a predetermined direction, the piston body 29 proceeds together with the threaded bar 28 in the direction of the distal end so as to push the oral composition contained in the container 23. With the screw type transmission mechanism 24, when a user rotates the rotational operation member 26 in a predetermined amount in use, the piston body 29 moves in accordance with the rotational amount of the rotational operation member 26. Therefore, when a small amount of the oral composition is desired to be ejected for use, an accurate amount of the oral composition can be pushed out. In addition, the oral composition can be prevented from dripping off from the nozzle or an application member. Further, every time the rotational operation member 26 is operated to rotate by a certain angle, a clicking sound is generated from the ratchet. Therefore, a desired amount of the oral composition can be discharged by counting the number of the clicking sounds.

The transmission mechanism of the oral composition is not limited to the embodiment. The pumping mechanisms as disclosed in Japanese Unexamined Patent Publication Nos. 2008-132099, Hei 3-261469 and Hei 9-2854477, mechanisms composed of a container having an elasticity as disclosed in U.S. Pat. Nos. 1,961,489, 3,199,510 and 3,391,696, or screw type transmission mechanisms as disclosed in Japanese Unexamined Patent Publication Nos. Hei 11-28120, 2001-57908 and 2000-300349, Japanese Unexamined Utility Model Publication Nos. Hei 8-858, Hei 7-44148 and Hei 5-72224, and Japanese Utility Model No. 3121384 may be used as the transmission mechanism. Further, a device having an electrical, or mechanical automatic driving pumping mechanism, a mechanism configured by connecting a separate container containing the oral composition as disclosed in Japanese Unexamined Patent Publication No. Hei 7-59801, or a mechanism having a tank attached to a main body as disclosed in Japanese Unexamined Patent Publication No. Hei 8-117254 may be also used.

Various compositions can be employed as the oral composition as long as the composition is a gel or cream oral care composition. For example, drug solutions containing an antimicrobial agent or an anti-inflammatory agent which is effective for the increase of blood flow or prevention and treatment of periodontitis, prophylactic and therapeutic agents for dental caries, prophylactic and therapeutic agents for hyperesthesia, prophylactic and therapeutic agents for stomatitis, an oral moisturizer, a denture stabilizing agent, a whitening component for a teeth whitening agent a sealant, a fluoride varnish, an oral anesthetic agent, and the like can be employed. Water-soluble gel compositions are more suitable in consideration of a dischargeability and applicability.

The neck portion 4 having a tapered cylindrical shape is provided with a fitting portion 4a at a distal end of the neck body 4 and a fitting portion 4b at a base end thereof. The fitting portion 4a is provided for detachably attaching the head body 3, and the fitting portion 4b is provided for coupling the neck body 4 to an upper end of the handle body 2. The supply path 11 for supplying the oral composition in the neck body 4 can be formed directly at the inner circumferential wall of the neck body 4. However, in the embodiment, a tube member 5 which is a separate member is provided at the interior of the neck body 4 so that the internal space of the tube member 5 serves as the supply path 11. The tube member 5 is configured to have an inner diameter of 1 to 2 mm, more preferably 1.3 to 1.7 mm, still more preferably approximately 1.6 mm. A distal end 5a of the tube member 5 is inserted to an attachment hole 42 formed at the distal end side of the neck body 4 in a closely contact manner, and a base end 5b thereof is inserted to an attachment hole 21 formed at the upper end side of the handle body 2 also in a closely contact manner.

Figure 4:
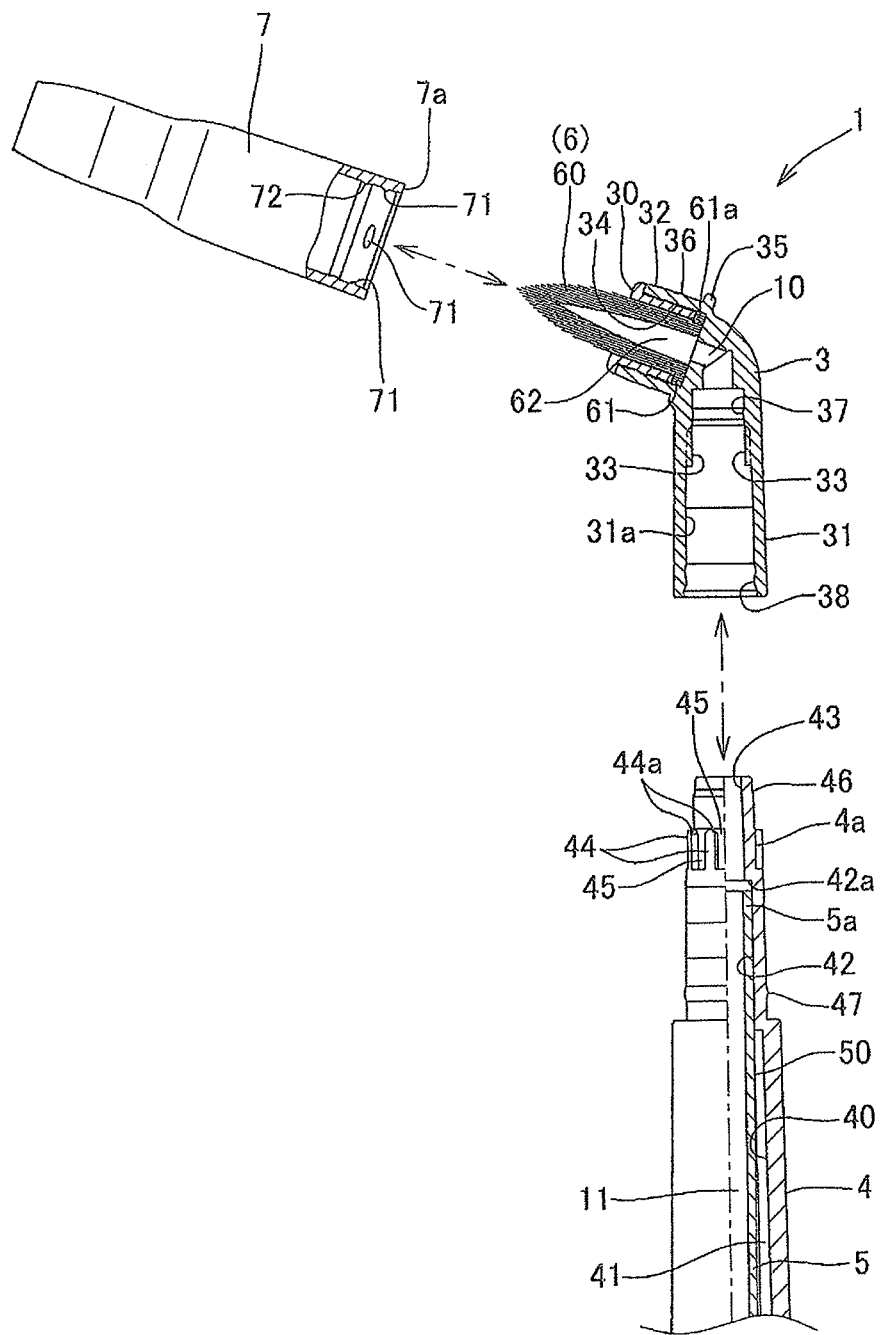
FIG. 4 is a longitudinal cross-sectional view illustrating a coupling configuration among a neck body, a head body, and a cap of the oral care instrument in FIG. 1.

The attachment hole 42 at the deep side (distal end side) is a through hole communicating with an introduction path 43 introducing the oral composition to the nozzle portion 10 of the head body 3 through a step portion 42a as shown in FIG. 4. The distal end 5a of the tube member 5 hits the step portion 42a. In the same manner, the attachment hole 21 at the deep side (base end side) communicates with a transmission path 22 extending from a pumping mechanism of the handle body 2 through a step portion 21a, and the base end 5b of the tube member 5 hits at the step portion 21a. As described above, both of the step portions restrict the movement of the tube member 5 in the axial direction. The oral composition supplied from the transmission path 22 of the handle body 2 travels in the internal space of the tube member 5 as the supply path 11 to the distal end side, then travels to the head body 3 through the introduction path 43 and is discharged from the nozzle portion 10 into an application member 6.

Figure 3:
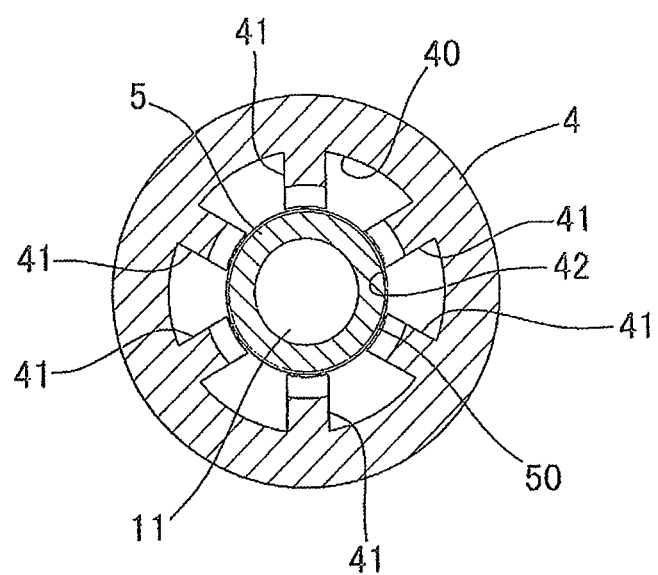
FIG. 3 is a cross-sectional view cut along a line A-A in FIG. 2.

As shown in FIGS. 2 to 4, a plurality of ribs 41 which are projected in the direction of a center axis and are extended long in the axial direction are provided at an inner circumferential wall 40 of the neck body 4. The ribs 41 provided at the same positions in the axial direction have a same projection height. A hypothetical inner diameter obtained by connecting the end faces of the projections of the ribs 41 in a circumferential direction (a diameter of a hypothetical circle which is surrounded by the end faces of the projections of the ribs 41 and is in contact with the end faces of the projections) is set to be gradually smaller toward the distal end side in the axial direction. Further, the ends of the ribs 41 at the distal end side of the neck body 4 are formed to be continuous with the attachment hole 42 such that the inner diameter is substantially identical to the inner circumferential face of the attachment hole 42. Accordingly, when the tube member 5 is assembled inside the neck body 4 by inserting the tube member 5 from the base end side of the neck body 4, the distal end 5a of the tube member 5 is guided into the attachment hole 42 without a hindrance in a state where an outer circumferential face 50 of the tube member 5 is supported by the end faces of the ribs 41. Therefore, the assembling operation can be easily performed without fail. Further, the strength of the neck body 4 can be increased by providing the plurality of ribs 41 so that the thickness of the neck body 4 can be reduced in comparison with that without the ribs, and the external shape of the neck body 4 can be made slimmer.

Figure 5:
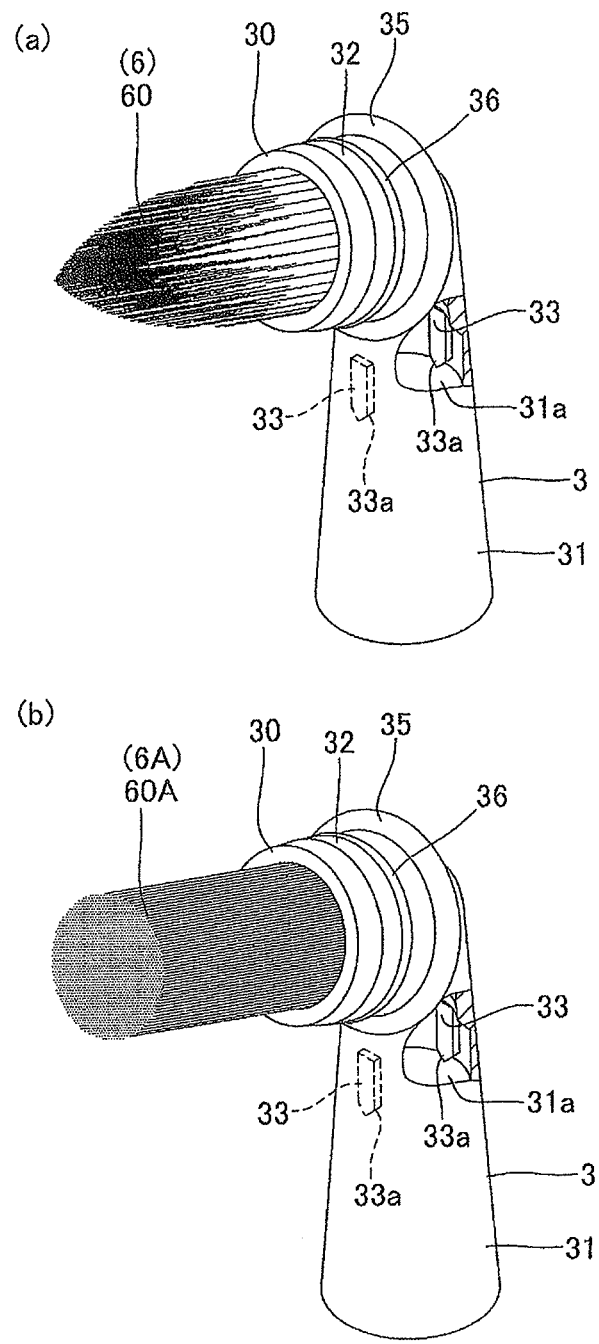
FIG. 5(a) is a partially cutaway perspective view of the head body of the oral care instrument and FIG. 5(b) is a partially cutaway perspective view of a head body of another embodiment in which a shape of a bundle is changed.

As shown in FIGS. 4 and 5, the head body 3 is detachably coupled to the neck body 4. The nozzle portion 10 for discharging the oral composition is provided at the distal end of the head body 3. The application member 6 formed of a bundle 60 of filaments is provided at the nozzle portion 10. The oral composition discharged from the nozzle portion 10 is supplied into the bundle 60 so that the oral composition is effectively applied to a site in the oral cavity through the bundle 60. In the embodiment, the head body 3 includes a straight attachment portion 31 which is to be attached to the distal end of the neck body 4 and a cylindrical attachment portion 32 which is bent at the distal end side thereof in a predetermined direction with respect to the attachment portion 31. Accordingly, the head body 3 is formed into a bent shape as a whole. In the head body 3 shown in FIG. 4, the bending angle of the head body 3 is set at 110°. In this regard, it is desirable that the bending angle of the head body 3 is set in the range of 80° to 130° and preferably in the range of 85° to 120° in consideration of workability in the oral composition applying operation by the application member 6. Further, as described later, even in a case where a brush body 81 for cleaning interdental spaces is provided with respect to the head body 3 instead of the application member 6, it is desirable that the bending angle of the head body 3 is set in the same range as that in the case where the application member 6 is provided. However, the head body 3 may have a straight shape or other shapes except the substantially dog-leg shape as described above. A fitting sealing configuration for fitting the head body 3 to the distal end of the neck body 4 in a tightly sealed manner is as follows. That is, as shown in FIG. 4, circular projections 46, 47 and circular projections 37, 38 which are engaged with each other, in a closely attached manner, are provided. Here, the circular projections 46, 47 are provided on the outer circumferential face at two positions of the distal end of the neck body 4 in the axial direction. The circular projections 37, 38 are provided at positions corresponding to the circular projections 46, 47, respectively, on the inner circumferential wall of the fitting hole 31a of the head body 3 to which the distal end of the neck body 4 is fitted.

If the head body 3 has the substantially dog-leg shape, there is a possibility that the head body 3 rotates about the axis of the neck body 4 when a large force is applied to the head body 3, thereby resulting in that the application member 6 is moved away from the site to which the oral composition should be applied. Then, a mechanism for stopping the rotation is provided at a coupling portion of the head body 3 and the neck body 4 in the embodiment. To be specific, a plurality of projections 44 are provided on the outer circumferential face of the fitting portion 4a of the neck body 4 with intervals in the circumferential direction. On the other hand, convex portions 33 are provided on the attachment portion 31 of the head body 3 at corresponding positions to concave grooves 45 on the inner circumferential wall of the fitting hole 31a to which the fitting portion 4a is inserted. Each convex portion 33 is engaged with the concave groove 45 formed between the projections 44, 44 so as to be opened in the distal end direction. With this configuration, when the fitting portion 4a at the distal end of the neck body 4 is coupled to the fitting hole 31a of the head body 3 by inserting the fitting portion 4a, the convex portions 33 are engaged with the projections 44, resulting in as a stopper of the rotation.

Figure 6:
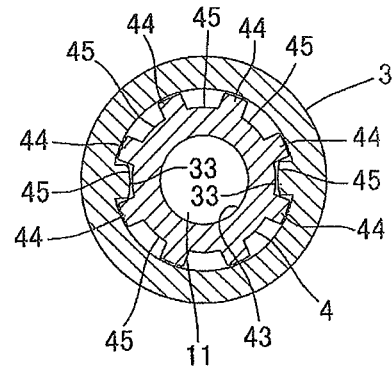
FIG. 6 is a cross-sectional view cut along a line B-B in FIG. 2.

In the embodiment, as shown in FIG. 6, two convex portions 33, 33 are provided at the corresponding positions on the inner circumferential wall of the fitting hole 31a, and a plurality of projections 44 are provided on the outer circumferential face of the fitting portion 4a so that a plurality of pairs of the concave grooves 45, 45 are formed in the rotational direction. Here, the two convex portions 33, 33 are horizontally opposed to each other and each pair of the concave grooves 45, 45 is horizontally opposed to each other. And the convex portions 33, 33 are fitted to the concave grooves 45, 45, respectively. Therefore, the application member 6 of the head body 3 can be directed to a plurality of directions by selecting a pair of the concave grooves 45, 45 with which the convex portions 33, 33 are engaged. With this configuration, in particular, when a pressing button of a pumping mechanism is provided on the handle body 2, a user can attach the head body 3 to the neck body 4 by selecting a positional relationship between the pressing button and a projecting direction of the application member 6 among a plurality of directions in a user-friendly manner. To be more specific, the user can appropriately select the positional relationship between the pressing button and the projecting direction of the application member 6 to a convenient direction for use in accordance with hand dominance and a location of a site to be applied in the oral cavity.

The forms such as the number of the concave grooves 45 and convex portions 33 as a stopper of the rotation are not limited to the embodiment. For example, if only one convex portion 33 and a plurality of concave groove 45 are provided, the angle of the head body 3 with respect to the neck body 4 can be changed in the same manner, which is a preferable embodiment. In addition, although the angle of the head body 3 with respect to the neck body 4 cannot be changed, a configuration with one convex portion 33 and one concave groove 45 can be also used as a stopper of the rotation. In a preferable embodiment, three or more of both the convex portions 33 and the concave grooves 45 are provided. Moreover, the number of the convex portions 33 is the same as that of the concave grooves 45 in a preferable embodiment. Thus, if three or more of the convex portions 33 and the concave grooves 45 are provided under a condition where the number of the convex portions 33 is same as that of the concave grooves 45, the convex portions 33 and the concave grooves 45 can be prevented from being damaged even when a user mistakenly twists the head body 3 and the neck body 4.

The width of the concave grooves 45 are set to be substantially the same as that of the convex portions 33 so as not to be unstable in the rotational direction when coupled. As shown in FIGS. 4 and 5, one or both of side ends 44a and side ends 33a, which are opposed to each other in the axial direction when coupled, are formed in a V tapered shape in order that the convex portions 33 can be engaged with the concave grooves 45 without a hindrance. Here, the side ends 44a are positioned on the projections 44 at the distal end side of the neck body in the axial direction. The side ends 33a are positioned on the convex portions 33 at the base end side of the head body in the axial direction. This can prevent a problem that the convex portions 33 and the concave grooves 45 cannot be engaged with each other successfully or are engaged with each other insufficiently because they hit each other. Further, the user can easily perform attachment and detachment operations without fail, and the head body 3 can be prevented from being detached from the neck body 4 during use.

Although one or both of the side ends 44a and the side ends 33a are formed in a V tapered shape in the embodiment, the shape may be a trapezoidal shape or a knife-like shape having a slope at one side. When both of the side ends 44a and the side ends 33a are formed in a trapezoidal shape or a knife-like shape, the side ends 44a should have sloping surfaces at opposite sides to those of the side ends 33a along the rotational direction such that the sloping surfaces are in contact with each other. A trapezoidal shape, a circular arch shape, or a shape obtained by forming an upper side of the trapezoid into a circular arch in combination of the trapezoidal shape and the circular arch may be employed. When the stopper configuration for rotation is omitted, a simple engagement configuration of a ring circular projection and a circular groove along the circumferential direction may be employed. Even in a case where the head body 3 has a straight shape, the head body 3 has a similar directionality depending on shapes of an application member at the distal end of the head body 3. Therefore, it is preferable that a similar stopper for rotation is provided in order to maintain a better application performance.

As shown in FIG. 5(a), the application member 6 is one tuft brush having only one bundle 60 of filaments and the distal end thereof has a conical shape. The application member 6 can clean contaminants in the oral cavity, and remove dental plaques from periodontal pockets, embrasures between interdentiums and alveolar ridges, or gingival marginal portions, while supplying the oral composition thereinto. In this regard, it is also possible to employ a bundle 60A of an application member 6A shown in FIG. 5(b). The bundle 60A is formed into a cylindrical shape by bundling a plurality of filaments and configured so as to clean tooth surfaces and smoothly apply the oral composition to tooth surfaces with a distal end face thereof. Further, the shape of the bundle and the configuration of the distal end of the application member can be appropriately designed according to a site to which the oral composition is applied. The application member 6 may be that of a toothbrush type having a plurality of bundles, or may be formed with various configurations other than the bundle. For example, the application member 6 may be formed with a bar-shaped elastomer or silicone rubber provided in a projection manner, an interproximal brush made of wires and filaments provided in a projection manner, a tongue brush, a sponge-like cleaning body, fabrics such as felt, cotton, gauze, and non-woven fabric, or others. The application member 6 may be formed with a simple bar nozzle provided.

Figure 7:
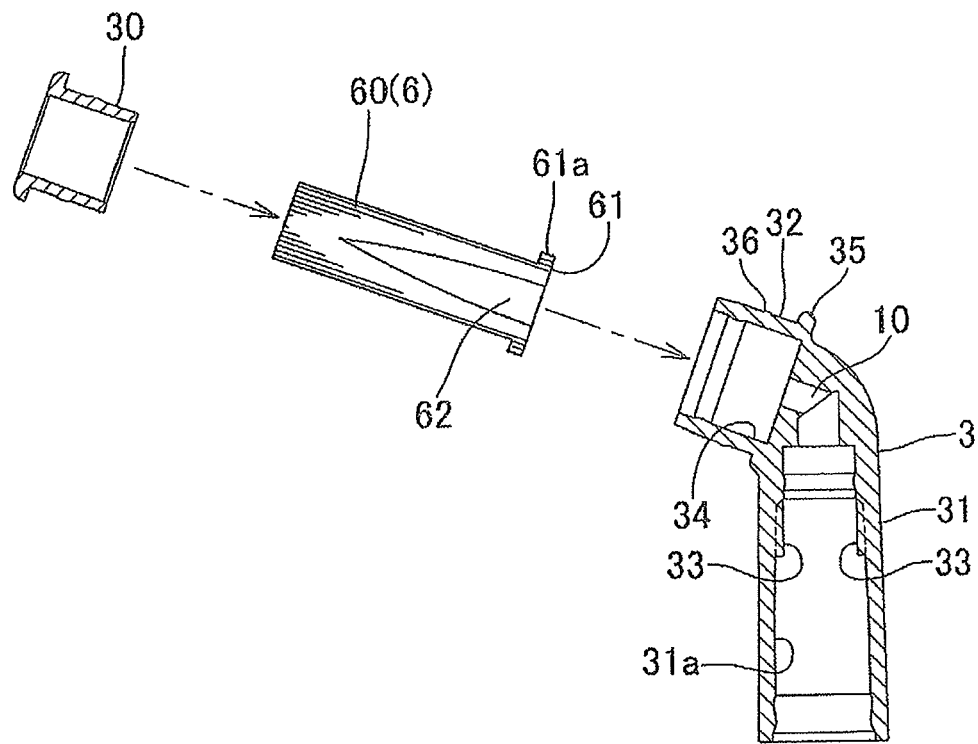
FIG. 7 is an exploded cross-sectional view illustrating a configuration in which an application member is attached to the head body in the oral care instrument in FIG. 1.

As shown in FIG. 7, the bundle 60 as the application member 6 is attached together with an application member stopper member 30 to the attachment hole 34 formed on an attachment portion 32 of the head body 3, and fixed by fitting the application member stopper member 30 to the attachment hole 34. Here, a distal end of the attachment hole 34 is opened. To be more specific, a plurality of filaments constituting the bundle 60 are integrally fused with each other at the base ends thereof, a base 61 having a swelled portion 61a swelled outward is provided, a communicating hole 62 communicating with an opening of the nozzle portion 10 is provided on the base 61. With this configuration, the ring stopper member for the application member 30 is attached, fitted and fixed to the attachment hole 34 together with the bundle 60 in a state where the ring stopper member for the application member 30 is attached from the distal end side of the bundle 60 to the exterior of the bundle 60 so as to be locked to the swelled portion 61a on the base 61. The distal end of the bundle 60 is trimmed into a tapered shape in a state where the application member 6 is fixed to the head body 3 in this manner. The trimming treatment can also be carried out before the application member 6 is attached to the head body 3. In this regard, it is also possible to use the bundle 60 without being trimmed into a tapered shape as the bundle 60A of the application member 6A shown in FIG. 5(b).

The nozzle portion 10 is opened on the bottom of the attachment hole 34 and the bundle 60 is fixed to the attachment hole 34. Therefore, as shown in FIG. 4, the oral composition discharged from the nozzle portion 10 is supplied into the bundle 60 through the communicating hole 62. With the configuration, the application member 6 formed of the bundle 60 can be easily assembled without fail so that it is advantageous in terms of automated manufacturing, and the filaments constituting the bundle 60 can be prevented from being fallen. As described above, a configuration in which the oral composition can be supplied into the application member 6 from the nozzle portion 10 is employed in the embodiment. However, another configuration is also preferable as described in Japanese Unexamined Patent Publication No. 2008-132099. Specifically, in the configuration, a nozzle portion for ejecting an oral composition toward an outer circumferential face of the application member in an oblique direction is opened at an outer circumferential face of the head body in the vicinity of the base of the application member 6 so as to make the oral composition apply to the outer circumferential face of the application member.

The cap 7 is a cap for protection against desiccation, and the distal end of the cap 7 is occluded. To be more specific, the cap 7 occludes the application member 6 and the nozzle portion 10 of the head body 3 to prevent the deterioration of the oral composition, and the desiccation and solidification of the oral composition remaining in each part (application member, nozzle portion, supply path) and the oral composition in the container. The cap 7 has a configuration capable of being attached to each of the distal ends of the head body 3 and the neck body 4 as shown in FIGS. 4 and 8. The cap 7 has a sealing configuration for occluding the cap-attached head body 3 and neck body 4 into a tightly sealed state when the cap 7 is attached to each of the distal ends of the head body 3 and the neck body 4.

As shown in FIG. 4, a flange portion 35 which the opening end 7a of the cap 7 hits, and a circular projection 36 for locking projections 71 formed in the vicinity of the opening ends on the inner circumferential face of the cap 7 are provided on the attachment portion 32 at the distal end of the head body 3. Further, a circular sealing projection 72 is formed on a position of the deep side (distal end side) with respect to the projections 71 on the inner circumferential face of the cap 7. Here, the circular sealing projection 72 serves as a sealing function by firmly adhering to the outer circumferential face of the attachment portion 32 of the head body 3 when attached. Further, as shown in FIG. 8, a circular step portion 73 which the projections 44 of the neck body 4 hits is provided at the deep side of the inner circumferential face of the above cap 7. In addition, a circular sealing projection 74 serving as a sealing function by firmly adhering to the outer circumferential face of the fitting portion 4a of the neck body 4 is formed at the opening end side with respect to the circular step portion 73.

As materials of each component including the handle body 2, the head body 3 excluding the application member 6, the neck body 4 and the tube member 5 provided inside the neck body 4, for example, synthetic resins such as polyolefin resins such as polypropylene and polyethylene, a polyamide resin, a polyester resin, a polycarbonate resin, a polyacetal resin, an ABS resin, a PS resin, a blended resin thereof, metals such as a glass and a stainless, or various other materials can be used.

Next, another embodiment of the oral care instrument in which a brush body for cleaning interdental spaces is provided at the distal end of the head body 3 instead of the application member 6 will be described. In this regard, the same members as those in the oral care instrument 1 of the above-described embodiment are denoted by the same reference numerals, and their detailed description is thus omitted.

Figure 9:
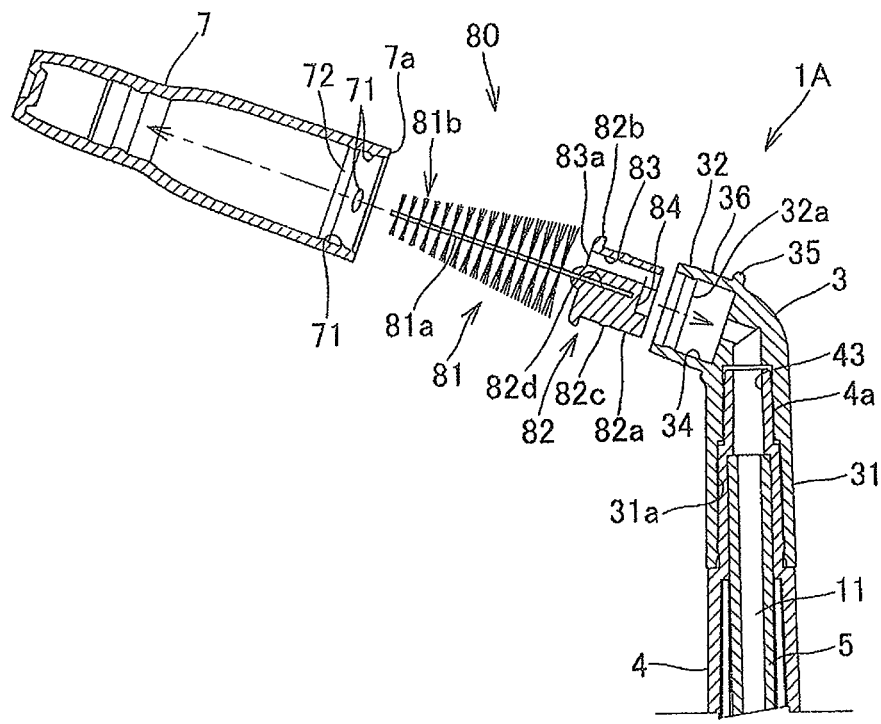
FIG. 9 is an exploded longitudinal cross-sectional view illustrating a coupling configuration among a neck body, a head body, an interdental brush member, and a cap of an oral care instrument in which the interdental brush member is provided instead of the application member.
Figure 10:
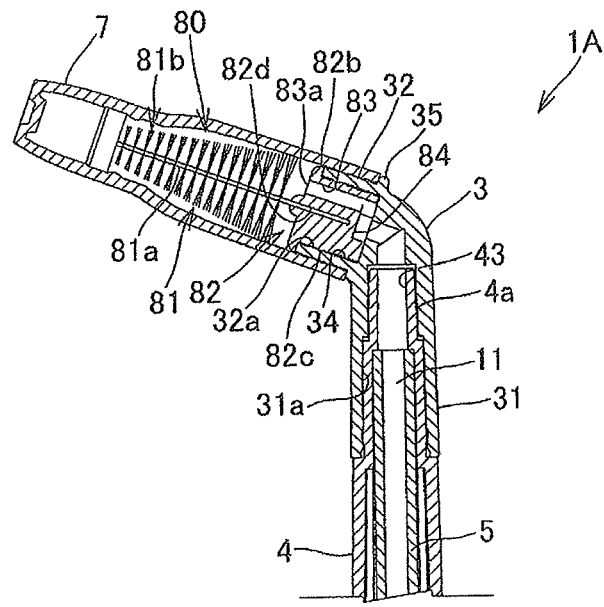
FIG. 10 is a longitudinal cross-sectional view illustrating the coupling configuration among the neck body, the head body, the interdental brush member, and the cap of the oral care instrument in FIG. 9.
Figure 11:
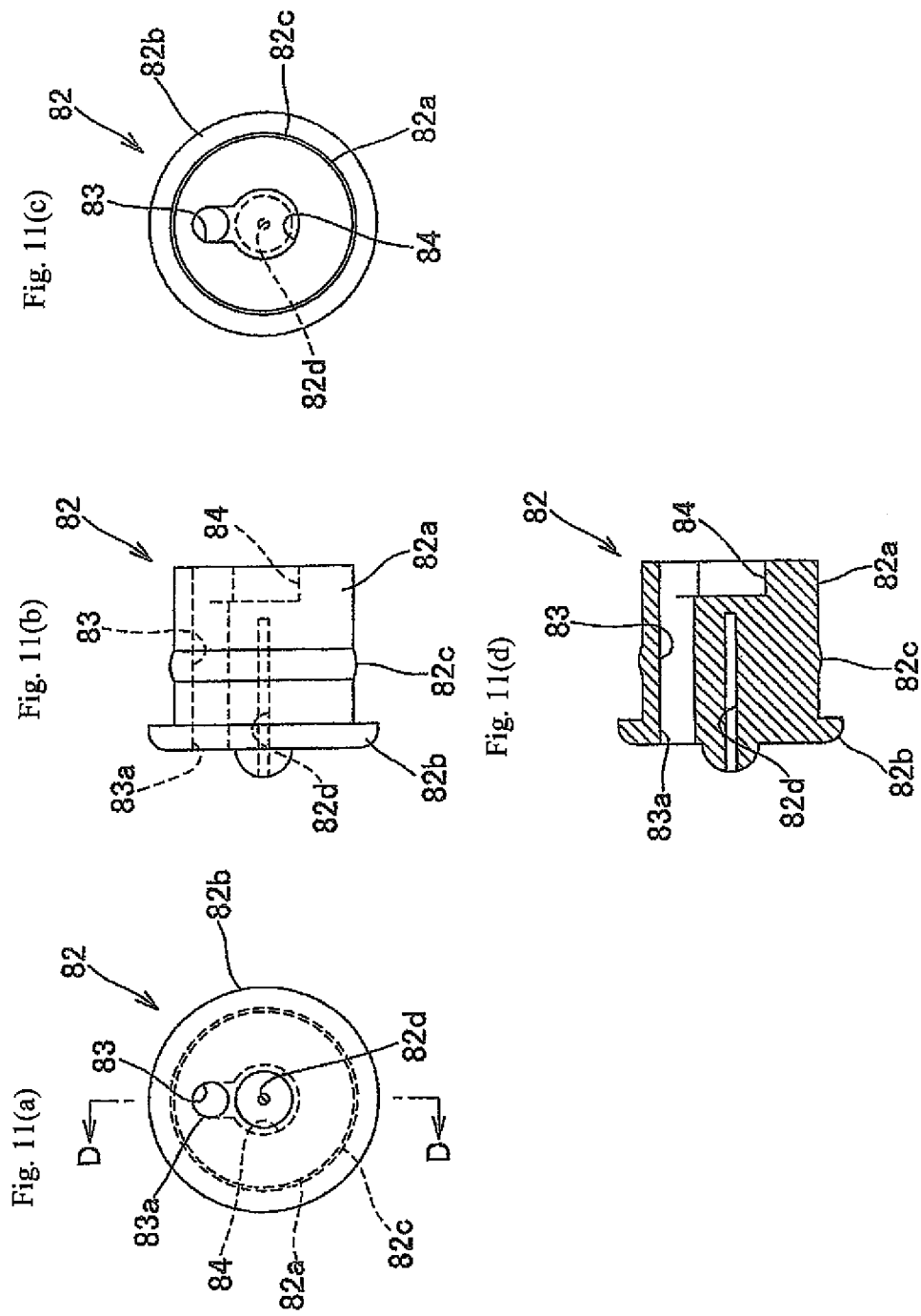
FIG. 11(a) is a left side view.
FIG. 11(b) is a front view.
FIG. 11(c) is a right side view of a brush supporting portion of the interdental brush member of the oral care instrument in FIG. 9.
FIG. 11(d) is a cross-sectional view cut along a line D-D in FIG. 11(a).

(1) In an oral care instrument 1A shown in FIGS. 9 to 11, an interdental brush member 80 having a brush body 81 and a brush supporting portion 82 for supporting the brush body 81 is detachably attached to the distal end of the head body 3 instead of the application member 6 and the application member stopper member 30.

The brush body 81 has a well-known structure and is provided with a core member 81a composed of a thin metal wire and a brush portion 81b in which a plurality of filaments are radially implanted into the core member 81a along the length direction thereof. The brush body 81 is manufactured in such a manner that a thin metal wire is bent in half, filaments are orthogonally placed between the doubled part of the thin metal wire, the thin metal wire is twisted so that the filaments are radially implanted into the core member 81a composed of the thin metal wire, and the filaments are then cut into a desired length. The outer shape of the brush portion 81b may be formed into a truncated cone shape as shown in FIG. 9, or may also be formed into a cylindrical shape or a barrel shape in which the outer diameter of a midway part in the length direction is set to be larger than the outer diameter of both ends thereof. Further, the size of the brush portion 81b can be appropriately changed. In this regard, it is also possible to employ the brush portion 81b which is configured in such a manner that filaments made of a synthetic resin or a synthetic rubber are radially and integrally formed on a core portion made of a synthetic resin or a metal.

The brush supporting portion 82 includes a main body portion 82a having a generally columnar shape, a circular flange 82b formed at a distal end of the main body portion 82a so as to be projected outward in the radial direction, and a circular projection 82c formed at a midway part in the length direction of the main body portion 82a so as to be projected outward in the radial direction. The length of the main body portion 82a is set to be substantially the same as the depth of the attachment hole 34. The outer diameter of the main body portion 82a is set to be substantially the same as the inner diameter of the attachment hole 34 of the head body 3. The outer diameter of the circular flange 82b is set to be substantially the same as the outer diameter of the attachment portion 32. The outer diameter of the circular projection 82c is set to be slightly larger than the outer diameter of the main body portion 82a. Further, a circular projection 32a which is projected toward the inside of the attachment hole 34 is formed at a midway part in the length direction of the attachment portion 32 of the head body 3. In this regard, the brush body 81 can be attached to the brush supporting portion 82 in an appropriate manner. The manner includes a method in which the core member 81a of the brush body 81 is attached to the brush supporting portion 82 by insert molding when forming the brush supporting portion 82, a method in which an insertion hole 82d for inserting the core member 81a is formed in advance on the brush supporting portion 82 and the core member 81*a* is inserted into and secured in the insertion hole 82*d* of the brush supporting portion 82 by heat fusion so as to be attached thereto, and the like.

When the interdental brush member 80 is attached to the head body 3, the main body portion 82*a* of the brush supporting portion 82 is inserted and fitted into the inside of the attachment hole 34 of the head body 3 from a distal end side toward a deep side thereof until the circular flange 82*b* comes into contact with a distal end of the attachment portion 32. Accordingly, the circular projection 82*c* of the main body portion 82*a* climbs over the circular projection 32*a* of the attachment portion 32 to thereby be engaged with the circular projection 32*a*. In this state, the interdental brush member 80 is not easily detached by only an operating force in the pullout direction at the time of cleaning interdental spaces due to the engagement between the circular projection 82*c* and the circular projection 32*a*. The interdental brush member 80 is configured such that it can be detached from the head body 3 to be replaced by a pullout operation with a force larger than the operating force at the time of cleaning interdental spaces. In this regard, it is also possible that the brush supporting portion 82 is undetachably fitted with respect to the attachment portion 32, and the interdental brush member 80 is replaced together with the head body 3 when the brush portion 81*b* is deteriorated.

A communication path 83 is provided in the main body portion 82*a* at a position which is eccentric from a center of the main body portion 82*a* so as to extend from a distal end to a base end of the main body portion 82*a*. A groove 84 extending to a central portion of the main body portion 82*a* is formed at a base end of the communication path 83. The communication path 83 is configured to communicate with an introduction path 43 and a supply path 11 through the groove 84 in a state where the brush supporting portion 82 is attached to the head body 3. A nozzle portion 83*a* which is opened toward the brush portion 81*b* is formed at a distal end of the communication path 83. The oral composition is discharged from the nozzle portion 83*a* to the brush portion 81*b* through the supply path 11, the introduction path 43, the groove 84, and the communication path 83. Here, it is preferable that the nozzle portion 83*a* is opened above the core member 81*a* for preventing the discharged oral composition from being directly dropped. Further, it is also a preferred embodiment that a receiving portion for receiving the oral composition which has been discharged from the nozzle portion 83*a* is formed at the distal end of the main body portion 82*a* in a projecting manner below the opening of the nozzle portion 83*a*.

Figure 12:
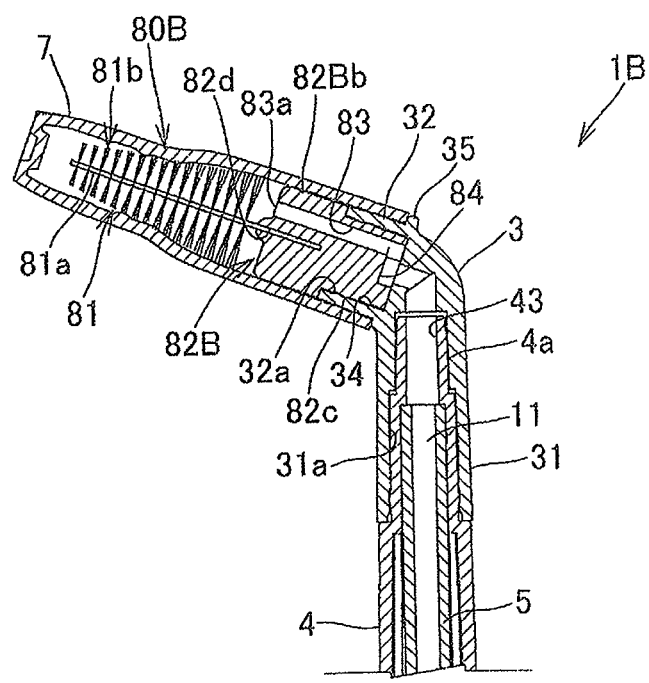
FIG. 12 is a longitudinal cross-sectional view illustrating a coupling configuration among the neck body, the head body, the interdental brush member, and the cap of the oral care instrument in FIG. 9 in which the structure of the brush supporting portion is partially changed.
Figure 13:
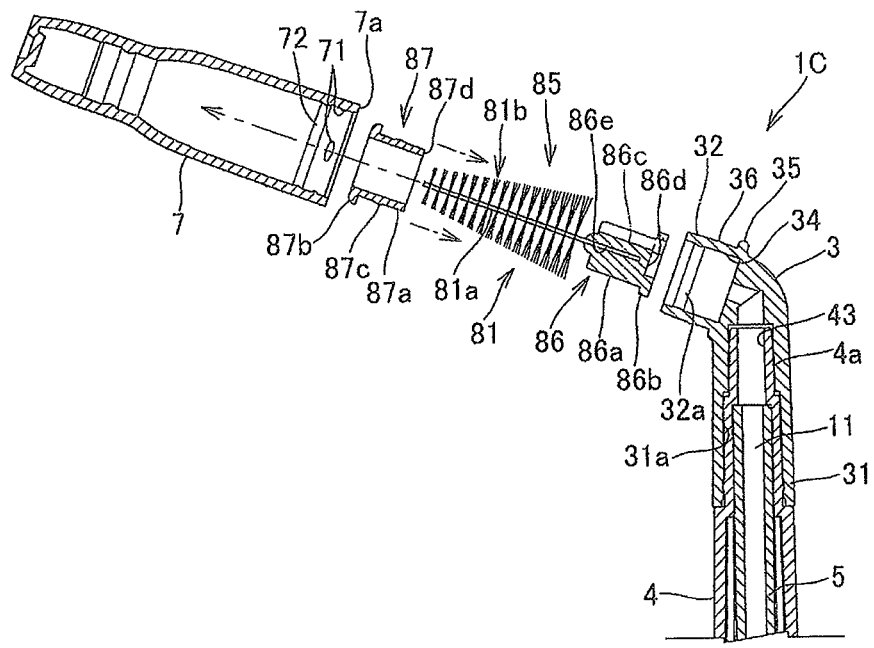
FIG. 13 is an exploded longitudinal cross-sectional view illustrating a coupling configuration among a neck body, a head body, an interdental brush member, a stopper member, and a cap of an oral care instrument provided with the interdental brush member having another structure.
Figure 14:
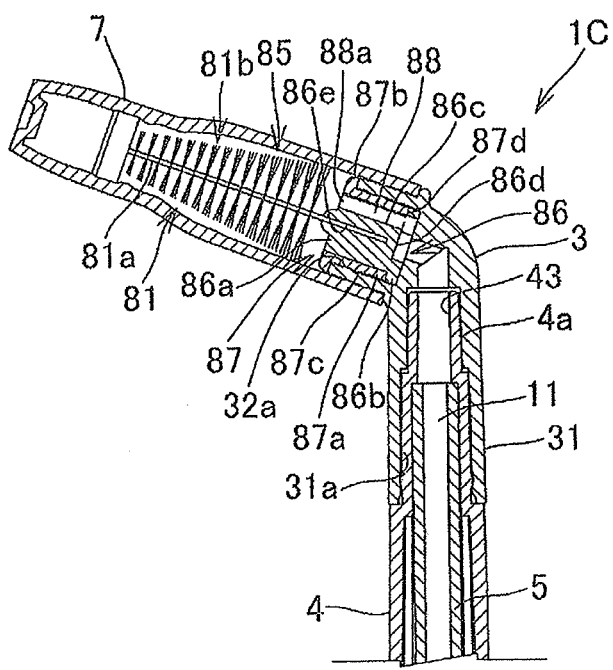
FIG. 14 is a longitudinal cross-sectional view illustrating the coupling configuration among the neck body, the head body, the interdental brush member, the stopper member, and the cap of the oral care instrument in FIG. 13.

In this regard, it is also a preferred embodiment that, as a brush supporting portion 82B in an interdental brush member 80B of an oral care instrument 1B shown in FIG. 12, the projecting length of a circular flange 82Bb from the main body portion 82*a* is set to be longer than that of the circular flange 82*b*, thereby making it possible to easily perform attachment and detachment operations of the interdental brush member 80B by pinching the circular flange 82Bb.

(2) In an oral care instrument 1C shown in FIGS. 13 to 16, an interdental brush member 85 having a brush body 81 and a brush supporting portion 86 for supporting the brush body 81 and a stopper member 87 for detachably fixing the interdental brush member 85 to the attachment portion 32 of the head body 3 are provided at the distal end of the head body 3 instead of the application member 6 and the application member stopper member 30.

The stopper member 87 includes a cylindrical body portion 87*a*, a circular flange 87*b* formed at a distal end of the body portion 87*a* so as to be projected outward in the radial direction, and a circular projection 87*c* formed at a midway part in the length direction of the body portion 87*a* so as to be projected outward in the radial direction. The outer diameter of the body portion 87*a* is set to be substantially the same as the inner diameter of the attachment hole 34. The length of the body portion 87*a* is set to be slightly shorter than the depth of the attachment hole 34. The outer diameter of the circular flange 87*b* is set to be substantially the same as the outer diameter of the attachment portion 32. The outer diameter of the circular projection 87*c* is set to be slightly larger than the outer diameter of the body portion 87*a*.

The brush body 81 has a well-known structure and is provided with a core member 81*a* composed of a thin metal wire and a brush portion 81*b* in which a plurality of filaments are radially implanted into the core member 81*a* along the length direction thereof as in the oral care instrument 1A.

Figure 15:
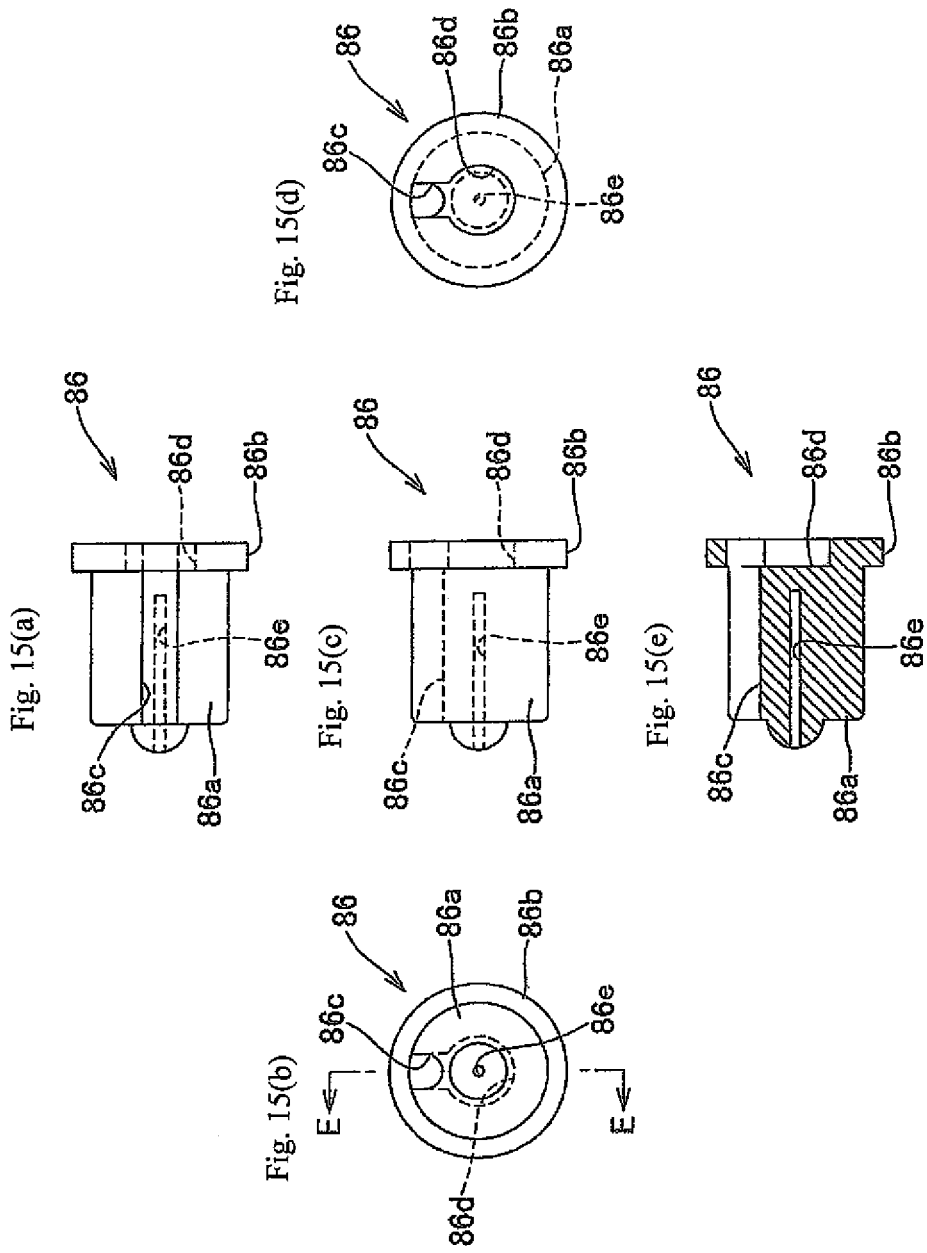
FIG. 15(a) is a plan view.
FIG. 15(b) is a left side view.
FIG. 15(c) is a front view.
FIG. 15(d) is a right side view of a brush supporting portion of the interdental brush member of the oral care instrument in FIG. 13.
FIG. 15(e) is a cross-sectional view cut along a line E-E in FIG. 15(b).
Figure 16:
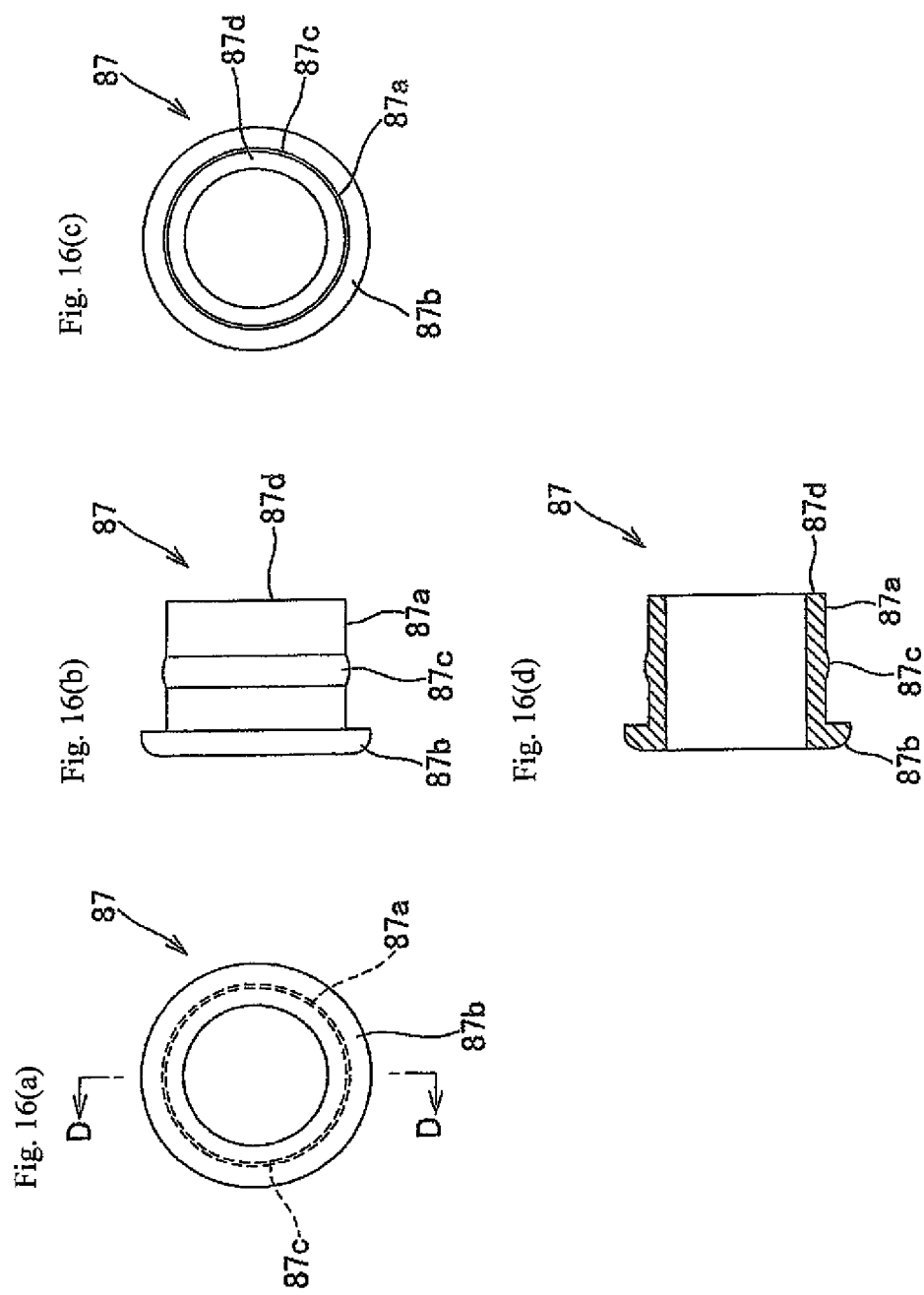
FIG. 16(a) is a left side view.
FIG. 16(b) is a front view.
FIG. 16(c) is a right side view of the stopper member of the oral care instrument in FIG. 13.
FIG. 16(d) is a cross-sectional view cut along a line D-D in FIG. 16(a).

The brush supporting portion 86 includes a main body portion 86*a* having a generally columnar shape and a circular locking portion 86*b* formed on an outer circumferential face of a base end of the main body portion 86*a* so as to be projected outward in the radial direction. The outer diameter of the main body portion 86*a* is set to be substantially the same as the inner diameter of the stopper member 87. The length of the main body portion 86*a* is set to be substantially the same as the length of the stopper member 87. The outer diameter of the locking portion 86*b* is set to be substantially the same as the inner diameter of the attachment hole 34 of the head body 3. A circular projection 32*a* which is projected toward the inside of the attachment hole 34 is formed at a midway part in the length direction of the attachment portion 32 of the head body 3. In this regard, the brush body 81 can be attached to the brush supporting portion 86 in an appropriate manner. The manner includes a method in which the core member 81*a* of the brush body 81 is attached to the brush supporting portion 86 by insert molding when forming the brush supporting portion 86, a method in which an insertion hole 86*e* for inserting the core member 81*a* is formed in advance on the brush supporting portion 86 and the core member 81*a* is inserted into and secured in the insertion hole 86*e* of the brush supporting portion 86 by heat fusion so as to be attached thereto as shown in FIG. 15, and the like.

When the interdental brush member 85 is attached to the head body 3, the brush supporting portion 86 is attached to the attachment hole 34 of the head body 3 and the stopper member 87 is inserted and fitted between the attachment portion 32 of the head body 3 and the brush supporting portion 86 until the circular flange 87*b* comes into contact with the distal end of the attachment portion 32. In this state, the circular projection 87*c* of the stopper member 87 climbs over the circular projection 32*a* of the attachment portion 32 to thereby be engaged with the circular projection 32*a*. In addition to this, the locking portion 86*b* of the brush supporting portion 86 is placed between an engagement portion 87*d* at the base end of the body portion 87*a* and a deep end face of the attachment hole 34. When a force in the pullout direction is applied to the interdental brush member 85, the locking portion 86*b* of the brush supporting portion 86 comes into contact with the engagement portion 87*d* of the stopper member 87 so that the interdental brush member 85 is undroppably held in the head body 3 through the stopper member 87. Meanwhile, when the interdental brush member 85 is replaced due to deterioration and the like of the brush portion 81*b*, the stopper member 87 is first removed and the interdental brush member 85 is then detached to be replaced. In this regard, it is also possible that the brush supporting portion 86 is undetachably fixed with respect to the attachment portion 32 by the stopper member 87, and the interdental brush member 85 is replaced together with the head body 3 when the brush portion 81b is deteriorated.

A groove 86c is provided on an outer circumferential face of the main body portion 86a so as to extend from the distal end to the base end of the main body portion 86a. A groove 86d extending to a central portion of the main body portion 86a is provided in a concave manner at a base end of the groove 86c. In a state where the interdental brush member 85 and the stopper member 87 are attached to the head body 3, the groove 86c and the groove 86d form a communication path 88 which extends from the distal end to the base end of the main body portion 86a and communicates with the introduction path 43 and the supply path 11. A nozzle portion 88a which is opened toward the brush portion 81b is formed at a distal end of the communication path 88. The oral composition is discharged from the nozzle portion 88a to the brush portion 81b through the supply path 11, the introduction path 43, and the communication path 88. In this regard, it is also possible that a concave-convex fitting portion or the like for positioning a fitting position of the main body portion 86a with respect to the attachment portion 32 in the circumferential direction is formed so that the nozzle portion 88a is constantly opened above the core member 81a for preventing the discharged oral composition from being directly dropped. Further, it is also a preferred embodiment that a receiving portion for receiving the oral composition which has been discharged from the nozzle portion 88a is formed at the distal end of the main body portion 86a in a projecting manner below the opening of the nozzle portion 88a.

In the oral care instrument 1C, the number of parts is increased in comparison with the oral care instruments 1A and 1B due to the provision of the stopper member 87. However, the oral care instrument 1C is preferable because it can effectively prevent the interdental brush member 85 from being detached from the attachment portion 32 of the head body 3. In the interdental brush member 85, the angle of the brush portion 81b is adjusted by bending the core member 81a at the vicinity of the main body portion 86a. Therefore, it is preferable that the main body portion 86a is made of a synthetic resin material which is softer than the head body 3 in order to prevent the core member 81a from being fractured at the bent portion and increase the durability of the interdental brush member 85. However, when the main body portion 86a is made of a soft synthetic resin material in this way, the main body portion 86a becomes more likely to be elastically deformed. In such a case, if there is only the engagement between both of the circular projections 82c and 32a as in the oral case instruments 1A and 1B, the pullout strength of the interdental brush members 80 and 80B is decreased. On the other hand, in the oral care instrument 1C, the stopper member 87 is locked with the head body 3 by means of the engagement between both of the circular projections 87c and 32a. Here, since the stopper member 87 can be made of a hard synthetic resin material as with the head body 3, the pullout strength of the stopper member 87 with respect to the head body 3 can be sufficiently ensured. In addition to this, also in the main body portion 86a, the pullout strength of the main body portion 86a can also be sufficiently ensured because the flange-like locking portion 86b is locked with the engagement portion 87d at the base end of the stopper member 87. Therefore, it is possible to easily increase the pullout strength of the interdental brush member 85.

Figure 17:
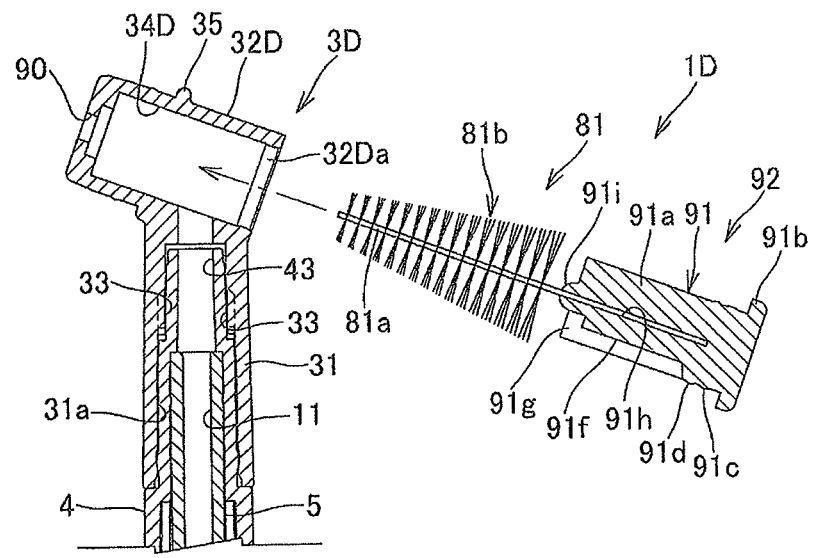
FIG. 17 is an exploded longitudinal cross-sectional view illustrating a coupling configuration among a head body and an interdental brush member of an oral care instrument provided with the interdental brush member having yet another structure.
Figure 18:
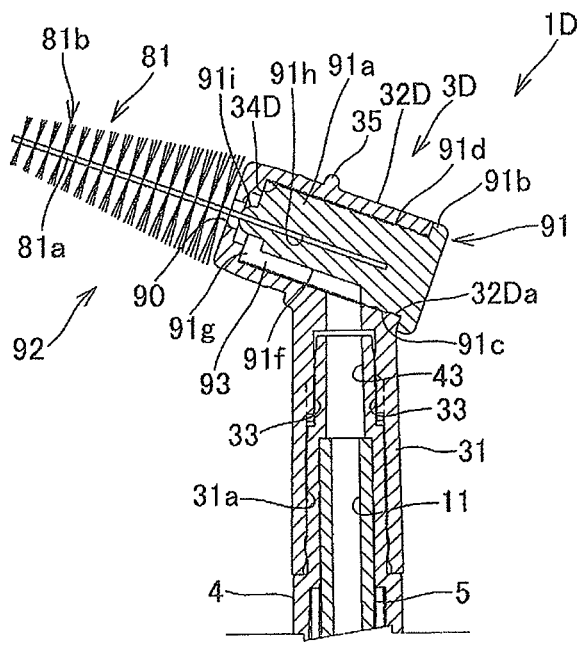
FIG. 18 is a longitudinal cross-sectional view illustrating the coupling configuration among the head body and the interdental brush member of the oral care instrument in FIG. 17.

(3) In an oral care instrument 1D shown in FIGS. 17 to 19, a head body 3D is used instead of the head body 3. In the head body 3D, a cylindrical attachment portion 32D is provided at an upper end of an attachment portion 31 in an inclined manner so that a distal end side of the attachment portion 32D is positioned above a base end side thereof. Further, an attachment hole 34D which is opened at a base end side thereof is formed inside the attachment portion 32D. Furthermore, a nozzle portion 90 having a diameter smaller than that of the attachment hole 34D is formed at the distal end side of the attachment portion 32D. Moreover, a circular projection 32Dc is formed at a base end of the attachment hole 34D so as to be projected inward. In addition to this, an interdental brush member 92 having a brush body 81 and a brush supporting portion 91 for supporting the brush body 81 is provided instead of the application member 6 and the application member stopper member 87, and the interdental brush member 92 is detachably fitted and fixed to the inside of the attachment portion 32D of the head body 3D by inserting the interdental brush member 92 into the attachment portion 32D from the base end side to the distal end side thereof.

The brush body 81 has a well-known structure and is provided with a core member 81a composed of a thin metal wire and a brush portion 81b in which a plurality of filaments are radially implanted into the core member 81a along the length direction thereof as in the oral care instrument 1A.

The brush supporting portion 91 includes a main body portion 91a having a generally columnar shape, a circular flange 91b formed on an outer circumferential face of a base end of the main body portion 91a so as to be projected outward in the radial direction, a circular projection 91c formed in the vicinity of the base end of the main body portion 91a so as to be projected outward in the radial direction, a circular sealing portion 91d formed at a distal end side of the vicinity of the base end of the main body portion 91a so as to be adjacent to the circular projection 91c and projected outward in the radial direction, and linear sealing portions 91e formed on the main body portion 91a from the circular sealing portion 91d to the distal end of the main body portion 91a with predetermined intervals in the circumferential direction of the main body portion 91a so as to be projected outward in the radial direction. The outer diameter of the main body portion 91a is set to be substantially the same as the inner diameter of the attachment hole 34. The length of the main body portion 91a is set to be substantially the same as the depth of the attachment hole 34. The outer diameter of the circular flange 91b is set to be substantially the same as the outer diameter of the attachment portion 32D. The outer diameter of the circular projection 91c is set to be slightly larger than the outer diameter of the main body portion 91a. The outer diameter of the circular sealing portion 91d and the outer diameter of the linear sealing portion 91e are set to be substantially the same as the outer diameter of the circular projection 91c. In this regard, the brush body 81 can be attached to the brush supporting portion 91 in an appropriate manner. The manner includes a method in which the core member 81a of the brush body 81 is attached to the brush supporting portion 91 by insert molding when forming the brush supporting portion 91, a method in which an insertion hole 91h for inserting the core member 81a is formed in advance on the brush supporting portion 91 and the core member 81a is inserted into and secured in the insertion hole 91h of the brush supporting portion 91 by heat fusion so as to be attached thereto as shown in FIG. 17, and the like.

When the interdental brush member 92 is attached to the head body 3, the brush portion 81b is inserted into the nozzle portion 90, and the main body portion 91a of the brush supporting portion 91 is inserted and fitted into the inside of the attachment hole 34 of the head body 3 from the base end side toward the distal end side thereof until the circular flange 91b comes into contact with a back end of the attachment portion 32D. In this state, the circular projection 91c of the main body portion 91a climbs over the circular projection 32Da of the attachment portion 32D to thereby be engaged with the circular projection 32Da. The interdental brush member 92 is not easily detached by only an operating force in a pushing direction at the time of cleaning interdental spaces due to the engagement between the circular projection 91c and the circular projection 32Da. The interdental brush member 92 is configured such that it can be detached from the head body 3 to be replaced by an operation in the pushing direction with a force larger than the operating force at the time of cleaning interdental spaces. In this regard, it is also possible that the brush supporting portion 91 is undetachably fitted with respect to the attachment portion 32D, and the interdental brush member 92 is replaced together with the head body 3 when the brush portion 81b is deteriorated.

A groove 91f is formed between the adjoining linear sealing portions 91e at a bottom part of the main body portion 91a so as to extend from the distal end of the main body portion 91a to the vicinity of the circular sealing portion 91d. A groove 91g extending to a central portion side of the main body portion 91a is formed at a distal end of the groove 91f. In a state where the brush supporting portion 91 is attached to the head body 3, a communication path 93 which communicates with the introduction path 43, the supply path 11, and the nozzle portion 90 is formed by the groove 91f and the groove 91g. The oral composition is discharged from the nozzle portion 90 to the brush portion 81b through the supply path 11, the introduction path 43, and the communication path 93. In this regard, it is preferable that a concave-convex fitting portion or the like for positioning the main body portion 91a with respect to the attachment portion 32D in the circumferential direction is formed between the attachment portion 32D and the main body portion 91a so that the groove 91f can be positioned at a lower side of the main body portion 91a, although it is not shown in the drawings. Further, it is also a preferred embodiment that a receiving portion for receiving the oral composition which has been discharged from the nozzle portion 90 is formed at the distal end of the main body portion 91a in a projecting manner below the opening of the nozzle portion 90. Furthermore, it is preferable that the opening diameter of the nozzle portion 90 is made to be large and a projection part 91i at the distal end of the main body portion 91a is made to be projected out of the nozzle portion 90. This makes it possible to change the attaching angle of the brush body 81 while preventing the core member 81a of the brush body 81 from being fractured by bending the projection part 91i when used.

According to the oral care instrument 1D, the detachment of the interdental brush member 92 in the pullout direction with respect to the head body 3 can be reliably prevented. Further, the oral composition can be discharged along the core member 81a of the brush body 81, thereby making it possible to effectively prevent the oral composition from being dropped.

Figure 20:
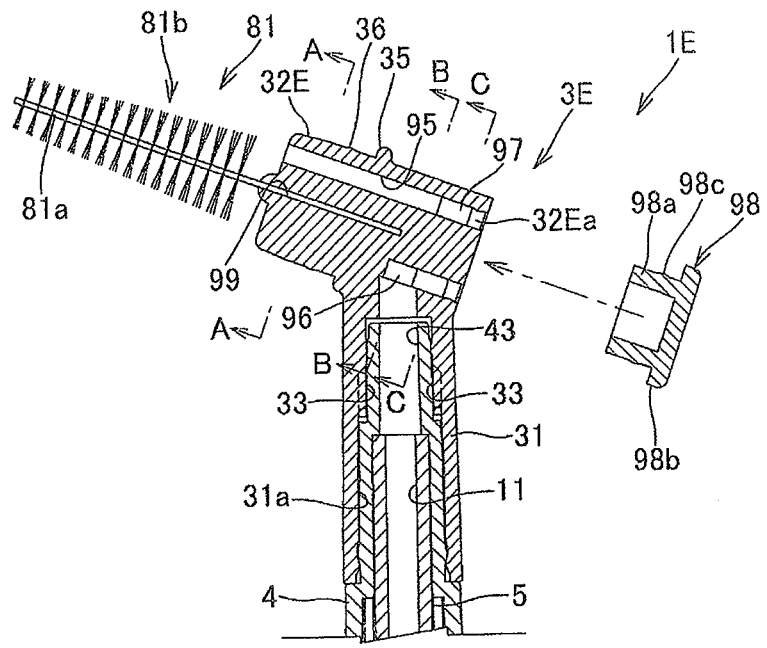
FIG. 20 is an exploded longitudinal cross-sectional view illustrating a coupling configuration among a head body and a lid member of an oral care instrument provided with an interdental brush member having yet another structure.
Figure 21:
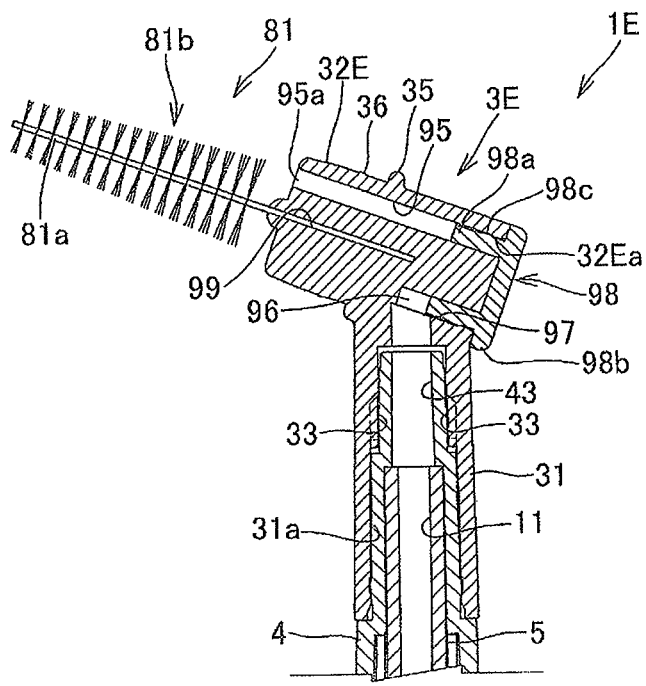
FIG. 21 is a longitudinal cross-sectional view illustrating the coupling configuration among the head body and the lid member of the oral care instrument in FIG. 20.

(4) In an oral care instrument 1E shown in FIGS. 20 to 22, instead of the application member 6 and the application member stopper member 87, a brush body 81 for cleaning interdental spaces is integrally provided in an attachment portion 32E of a head body 3E which is a substitute for the head body 3.

The brush body 81 has a well-known structure and is provided with a core member 81a composed of a thin metal wire and a brush portion 81b in which a plurality of filaments are radially implanted into the core member 81a along the length direction thereof as in the oral care instrument 1A.

In the head body 3E, the columnar attachment portion 32E is provided at an upper end of the attachment portion 31 in an inclined manner so that a distal end side of the attachment portion 32E is positioned above a base end side thereof. The brush portion 81b is arranged at the distal end side of the attachment portion 32E and a base portion of the core member 81a is buried in a central portion of the attachment portion 32E so that the brush body 81 is integrally provided in the head body 3E. A communication path 95 which passes through the attachment portion 32E in the axial direction is formed at an upper part of the attachment portion 32E from the distal end to the base end thereof. A nozzle portion 95a which is opened toward the brush portion 81b is formed at a distal end of the communication path 95. A semicircular groove 96 which communicates with the communication path 95 is formed in the vicinity of the base end of the attachment portion 32E. A circular groove 97 which is opened at a base end side thereof is formed at the base end of the attachment portion 32E so as to continue to the groove 96. A circular projection 32Ea which is projected to the inside of the circular groove 97 is formed at the base end of the attachment portion 32E. In this regard, the brush body 81 can be attached to the head body 3E in an appropriate manner. The manner includes a method in which the core member 81a of the brush body 81 is attached to the head body 3E by insert molding when forming the head body 3E, a method in which an insertion hole 99 for inserting the core member 81a is formed in advance on the head body 3E and the core member 81a is inserted into and secured in the insertion hole 99 of the head body 3E by heat fusion so as to be attached thereto as shown in FIG. 20, and the like.

A lid member 98 is detachably provided at the base end of the head body 3E. The lid member 98 is provided with a cylindrical portion 98a which is fitted and fixed to the inside of the circular groove 97, a circular flange 98b which is formed at a base end of the lid member 98, and a circular projection 98c which is formed in the vicinity of the base end of the cylindrical portion 98a so as to be projected outward in the radial direction.

In the oral care instrument 1E, in a state where the lid member 98 is attached to the head body 3E by fitting the cylindrical portion 98a of the lid member 98 into the circular groove 97, the circular projection 98c of the lid member 98 climbs over the circular projection 32Ea of the attachment portion 32E to thereby be engaged with the circular projection 32Ea. Accordingly, the lid member 98 is fitted and fixed to the attachment portion 32E in a liquid-tight state by the engagement between both of the circular projections 98c and 32Ea. In this state, the introduction path 43, the supply path 11, and the nozzle portion 95a are communicated with each other by the communication path 95 and the groove 96. Accordingly, the oral composition passes from the supply path 11, the introduction path 43, through the groove 96 and the communication path 95 in this order so as to be discharged from the nozzle portion 95a to the brush portion 81b.

In the oral care instrument 1E, although the brush body 81 needs to be replaced together with the head body 3E when the brush portion 81b is deteriorated, since the brush body 81 is integrally provided in the head body 3E, the detachment of the brush body 81 from the head body 3E can be reliably prevented.

Although the present embodiment has been described above, the present invention is not limited to the embodiment, and the invention can be applied to various forms without departing from a scope of the invention.

REFERENCE SIGNS LIST

1 Oral care instrument
2 Handle body
3 Head body
4 Neck body
4a Fitting portion
4b Fitting portion
5 Tube member
5a Distal end
5b Base end
6 Application member
7 Cap
7a Opening end
10 Nozzle portion
11 Supply path
21 Attachment hole
21a Step portion
22 Transmission path
23 Container
24 Screw type transmission mechanism
25 Main body
26 Rotational operation member
27 Holding member
28 Threaded bar
29 Piston body
30 Application member stopper member
31 Attachment portion
31a Fitting hole
32 Attachment portion
32a Circular projection
33 Convex portion
33a Side end
34 Attachment hole
35 Flange portion
36 Circular projection
37 Circular projection
38 Circular projection
40 Inner circumferential wall
41 Rib
42 Attachment hole
42a Step portion
43 Introduction path
44 Projection
44a Side end
45 Concave groove
46 Circular projection
47 Circular projection
50 Outer circumferential face
60 Bundle
61 Base
61a Swelled portion
62 Communicating hole
71 Projection
72 Sealing projection
74 Circular step portion
6A Sealing projection
6A Application member
60A Bundle
1A Oral care instrument
80 Interdental brush member
81 Brush body
81a Core member
81b Brush portion
82 Brush supporting portion
82a Main body portion
82b Circular flange
82c Circular projection
82d Insertion hole
83 Communication path
83a Nozzle portion
84 Groove
1B Oral care instrument
80B Interdental brush member
82B Brush supporting portion
82Bb Circular flange
1C Oral care instrument
85 Interdental brush member
86 Brush supporting portion
86a Main body portion
86b Locking portion
86c Groove
86d Groove
86e Insertion hole
87 Stopper member
87a Body portion
87b Circular flange
87c Circular projection
87d Engagement portion
88 Communication path
88a Nozzle portion
1D Oral care instrument
3D Head body
32D Attachment portion
32Da Circular projection
34D Attachment hole
90 Nozzle portion
91 Brush supporting portion
91a Main body portion
91b Circular flange
91c Circular projection
91d Circular sealing portion
91e Linear sealing portion
91f Groove
91g Groove
91h Insertion hole
91i Projection part
92 Interdental brush member
93 Communication path
1E Oral care instrument
3E Head body
32E Attachment portion
32E a Circular projection
95 Communication path
95a Nozzle portion
96 Groove
97 Circular groove
98 Lid member
98a Cylindrical portion
98b Circular flange
98c Circular projection
99 Insertion hole

The invention claimed is:

1. An oral care instrument for applying a gel or cream oral composition in an oral cavity by discharging the oral composition from a nozzle portion at a distal end of the instrument, comprising:
a handle body gripped when used;
a head body having the nozzle portion for discharging the oral composition at the distal end of the instrument; and
a neck body which is formed between the handle body and the head body and by which the head body can be inserted to deep portions in the oral cavity, wherein a supply path for supplying the oral composition from the handle body to the nozzle portion of the head body through an inner side of the neck body is provided, and the head body is detachably coupled to the neck body, wherein an application member formed of only one bundle of filaments is provided at the nozzle portion of the head body, wherein a base on which a plurality of filaments constituting the bundle are integrally fused with each other at base ends of the filaments is provided at a base end of the application member, and wherein a communicating hole at a base end of which communicates with an opening of the nozzle portion and a distal end of which extends toward a distal side of the application member is provided inside of the application member.

2. The oral care instrument according to claim 1,
wherein a plurality of ribs which are projected in the direction of a center axis and are extended long in the axial direction are provided on an inner circumferential wall of the neck body, and
a cylindrical tube member which has an inner diameter of 1 to 2 mm and constitutes the supply path of the oral composition is inserted and attached to the neck body in such a manner that an outer circumferential face of the tube member is supported by the plurality of ribs.

3. The oral care instrument according to claim 2, further comprising a cap detachably attached to each of a position at which a nozzle portion at the distal end side of the head body is covered and a position at which a distal end of the neck body is covered in a state where the head body is detached.

4. The oral care instrument according to claim 2,
wherein the head body is formed into a bent shape,
a plurality of projections are provided on the outer circumferential face of the distal end of the neck body with intervals in the circumferential direction,
convex portions which is engaged with concave grooves formed between the projections are provided at corresponding positions to the distal end of the neck body on the inner circumferential wall of the head body, and
when the distal end of the neck body is inserted and coupled to the head body, the convex portions are engaged with the projections, resulting in as a stopper of the rotation.

5. The oral care instrument according to claim 2, wherein a container containing an oral composition and a screw type transmission mechanism for pushing the oral composition out to a supply path are provided inside the handle body.

6. The oral care instrument according to claim 1,
wherein
a ring stopper member for the application member which is attached from the distal end side of the application member to the exterior of the application member so as to be locked to the swelled portion of the base is attached together with the application member to the circumference of the nozzle portion of the head body.

7. The oral care instrument according to claim 1, further comprising a cap detachably attached to each of a position at which the nozzle portion at the distal end side of the head body is covered and a position at which a distal end of the neck body is covered in a state where the head body is detached.

8. The oral care instrument according to claim 1,
wherein the head body is formed into a bent shape,
a plurality of projections are provided on the outer circumferential face of the distal end of the neck body with intervals in the circumferential direction,
convex portions which is engaged with concave grooves formed between the projections are provided at corresponding positions to the distal end of the neck body on the inner circumferential wall of the head body, and
when the distal end of the neck body is inserted and coupled to the head body, the convex portions are engaged with the projections, resulting in as a stopper of the rotation.

9. The oral care instrument according to claim 8,
wherein one or both of side ends on the projections at the distal end side of the neck body in the axial direction and side ends on the convex portions at the base end side of the head body in the axial direction are formed in a V tapered shape, the side ends on the projections and the side ends on the convex portions being opposed to each other in the axial direction when coupled.

10. The oral care instrument according to claim 1,
wherein a container containing an oral composition and a screw type transmission mechanism for pushing the oral composition out to a supply path are provided inside the handle body.

* * * * *